(12) United States Patent
Celermajer et al.

(10) Patent No.: US 8,882,697 B2
(45) Date of Patent: Nov. 11, 2014

(54) APPARATUS AND METHODS TO CREATE AND MAINTAIN AN INTRA-ATRIAL PRESSURE RELIEF OPENING

(75) Inventors: David Celermajer, Vaucluse (AU); Edward McNamara, Chelmsford, MA (US); Michael W. Sutherland, Pelham, NH (US); Hiroatsu Sugimoto, Cambridge, MA (US)

(73) Assignee: DC Devices, Inc., Tewksbury, MA (US)

( * ) Notice: Subject to any disclaimer, the term of this patent is extended or adjusted under 35 U.S.C. 154(b) by 0 days.

(21) Appl. No.: 13/370,913

(22) Filed: Feb. 10, 2012

(65) Prior Publication Data

US 2012/0259263 A1 Oct. 11, 2012

(51) Int. Cl.
*A61M 1/00* (2006.01)
*A61B 18/00* (2006.01)
(Continued)

(52) U.S. Cl.
CPC ........... *A61B 17/0057* (2013.01); *A61B 8/0883* (2013.01); *A61B 6/503* (2013.01); *A61N 7/022*
(Continued)

(58) Field of Classification Search
CPC ............. A61B 17/32075; A61B 2017/320064; A61B 2017/00592; A61B 17/3468; A61B 17/3494; A61B 17/3496; A61B 6/504; A61B 2017/320016; A61B 2017/320056; A61B 17/0057; A61B 17/32; A61B 17/320016; A61B 17/32053; A61B 6/503; A61B 2017/00252; A61B 2017/00575; A61B 18/1492; A61B 2018/00351; A61B 17/32002; A61B 2017/00247; A61B 18/12; A61B 18/14; A61B 18/1477; A61B 18/1487; A61B 2018/12; A61B 2018/14; A61B 2018/1407; A61B 2018/1417; A61B 2018/142; A61B 2018/1435; A61B 2018/1437; A61B 2018/144; A61B 2018/1475
USPC ......... 604/8, 9, 500, 506, 507, 508, 509, 510, 604/20, 22, 164.01, 164.09, 164.1, 164.11, 604/164.13, 171; 600/101, 104, 184; 606/27, 28, 29, 30, 31, 32, 33, 45
See application file for complete search history.

(56) References Cited

U.S. PATENT DOCUMENTS 4,018,228 A * 4/1977 Goosen ......................... 606/184
4,705,507 A 11/1987 Boyles
(Continued)

FOREIGN PATENT DOCUMENTS

AU  2007317191 A1  5/2008
CN  102905626 A    1/2013
(Continued)

OTHER PUBLICATIONS

European Application Serial No. 10772411, European Search Opinion and Supplementary European Search Report mailed Mar. 16, 2012, search completed Mar. 8, 2012, 5 pages.
(Continued)

*Primary Examiner* — Adam Marcetich
(74) *Attorney, Agent, or Firm* — Shay Glenn LLP

(57) ABSTRACT

The present disclosure relates to a method and a device for treating heart failure by normalizing elevated blood pressure in the left and right atria of a heart of a mammal The present disclosure includes methods for creating and maintaining an opening in the atrial septum. Tools for making an opening and enlarging the opening are also disclosed. Use of the techniques and tools described herein prolongs the patency of an intra-atrial pressure relief opening.

28 Claims, 11 Drawing Sheets

(51) Int. Cl.
  *A61B 17/34* (2006.01)
  *A61M 25/00* (2006.01)
  *A61M 29/02* (2006.01)
  *A61B 17/32* (2006.01)
  *A61B 17/3205* (2006.01)
  *A61B 8/08* (2006.01)
  *A61B 6/00* (2006.01)
  *A61N 7/02* (2006.01)
  *A61B 6/12* (2006.01)
  *A61B 17/00* (2006.01)
  *A61B 18/14* (2006.01)
  *A61B 17/22* (2006.01)

(52) U.S. Cl.
  CPC ............ (2013.01); *A61B 6/12* (2013.01); *A61B 2018/00351* (2013.01); *A61B 17/320016* (2013.01); *A61B 2017/3488* (2013.01); *A61B 2018/00577* (2013.01); *A61B 2017/00606* (2013.01); *A61B 17/32053* (2013.01); *A61B 2017/00247* (2013.01); *A61B 2017/00592* (2013.01); *A61B 2017/00575* (2013.01); *A61B 2017/00867* (2013.01); *A61B 17/3478* (2013.01); *A61B 2017/320004* (2013.01); *A61B 2017/320008* (2013.01); *A61B 2018/0022* (2013.01); *A61B 2017/00252* (2013.01); *A61B 8/0841* (2013.01); *A61B 17/32002* (2013.01); *A61B 18/1492* (2013.01); *A61B 17/32* (2013.01); *A61B 2017/22044* (2013.01)
  USPC .............. 604/8; 604/9; 604/500; 604/506; 604/20; 604/22; 604/164.01; 600/101; 600/104; 606/27; 606/28; 606/32; 606/33; 606/45

(56) References Cited

U.S. PATENT DOCUMENTS

| | | | |
|---|---|---|---|
| 5,108,420 A | 4/1992 | Marks | |
| 5,171,233 A | 12/1992 | Amplatz et al. | |
| 5,334,217 A | 8/1994 | Das | |
| 5,429,144 A | 7/1995 | Wilk | |
| 5,478,353 A * | 12/1995 | Yoon | 606/213 |
| 5,578,045 A | 11/1996 | Das | |
| 5,693,090 A | 12/1997 | Unsworth et al. | |
| 5,702,412 A * | 12/1997 | Popov et al. | 606/159 |
| 5,725,552 A | 3/1998 | Kotula et al. | |
| 5,824,071 A | 10/1998 | Nelson et al. | |
| 5,876,436 A | 3/1999 | Vanney et al. | |
| 5,893,369 A * | 4/1999 | LeMole | 606/184 |
| 6,050,936 A | 4/2000 | Schweich, Jr. et al. | |
| 6,077,281 A | 6/2000 | Das | |
| 6,123,715 A | 9/2000 | Amplatz | |
| 6,156,055 A | 12/2000 | Ravenscroft | |
| 6,190,353 B1 * | 2/2001 | Makower et al. | 604/95.01 |
| 6,193,734 B1 | 2/2001 | Bolduc et al. | |
| 6,258,119 B1 | 7/2001 | Hussein et al. | |
| 6,334,864 B1 | 1/2002 | Amplatz et al. | |
| 6,350,277 B1 | 2/2002 | Kocur | |
| 6,355,052 B1 | 3/2002 | Neuss et al. | |
| 6,355,056 B1 | 3/2002 | Pinheiro | |
| 6,383,195 B1 | 5/2002 | Richard | |
| 6,395,017 B1 | 5/2002 | Dwyer et al. | |
| 6,402,777 B1 | 6/2002 | Globerman et al. | |
| 6,409,716 B1 * | 6/2002 | Sahatjian et al. | 604/509 |
| 6,440,152 B1 | 8/2002 | Gainor et al. | |
| 6,454,795 B1 | 9/2002 | Chuter | |
| 6,458,153 B1 | 10/2002 | Bailey et al. | |
| 6,468,303 B1 | 10/2002 | Amplatz et al. | |
| 6,527,746 B1 | 3/2003 | Oslund et al. | |
| 6,579,311 B1 * | 6/2003 | Makower | 623/1.23 |
| 6,626,936 B2 | 9/2003 | Stinson | |
| 6,641,610 B2 | 11/2003 | Wolf et al. | |
| 6,645,143 B2 * | 11/2003 | VanTassel et al. | 600/300 |
| 6,666,885 B2 | 12/2003 | Moe | |
| 6,712,836 B1 | 3/2004 | Berg et al. | |
| 6,837,901 B2 | 1/2005 | Rabkin et al. | |
| 6,866,679 B2 | 3/2005 | Kusleika | |
| 6,911,037 B2 | 6/2005 | Gainor et al. | |
| 6,913,614 B2 | 7/2005 | Marino et al. | |
| 6,936,058 B2 | 8/2005 | Forde et al. | |
| 6,979,343 B2 | 12/2005 | Russo et al. | |
| 7,001,409 B2 | 2/2006 | Amplatz | |
| 7,097,653 B2 | 8/2006 | Freudenthal et al. | |
| 7,105,024 B2 | 9/2006 | Richelsoph | |
| 7,159,593 B2 | 1/2007 | McCarthy et al. | |
| 7,226,466 B2 | 6/2007 | Opolski | |
| 7,317,951 B2 | 1/2008 | Schneider et al. | |
| 7,338,514 B2 | 3/2008 | Wahr et al. | |
| 7,419,498 B2 | 9/2008 | Opolski et al. | |
| 7,445,630 B2 | 11/2008 | Lashinski et al. | |
| 7,473,266 B2 | 1/2009 | Glaser | |
| 7,485,141 B2 | 2/2009 | Majercak et al. | |
| 7,524,330 B2 | 4/2009 | Berreklouw | |
| 7,530,995 B2 | 5/2009 | Quijano et al. | |
| 7,625,392 B2 | 12/2009 | Coleman et al. | |
| 7,658,747 B2 | 2/2010 | Forde et al. | |
| 7,699,297 B2 | 4/2010 | Cicenas et al. | |
| 7,766,966 B2 | 8/2010 | Richelsoph | |
| 7,819,890 B2 | 10/2010 | Russo et al. | |
| 7,842,026 B2 | 11/2010 | Cahill et al. | |
| 7,871,419 B2 | 1/2011 | Devellian et al. | |
| 7,927,370 B2 | 4/2011 | Webler et al. | |
| 7,976,564 B2 | 7/2011 | Blaeser et al. | |
| 8,034,061 B2 | 10/2011 | Amplatz et al. | |
| 8,043,360 B2 | 10/2011 | McNamara et al. | |
| 8,048,147 B2 | 11/2011 | Adams | |
| 8,070,708 B2 | 12/2011 | Rottenberg et al. | |
| 8,091,556 B2 | 1/2012 | Keren et al. | |
| 8,157,860 B2 | 4/2012 | McNamara et al. | |
| 8,172,896 B2 | 5/2012 | McNamara et al. | |
| 8,252,042 B2 | 8/2012 | McNamara et al. | |
| 8,460,372 B2 | 6/2013 | McNamara et al. | |
| 2001/0029368 A1 * | 10/2001 | Berube | 606/33 |
| 2002/0029061 A1 | 3/2002 | Amplatz et al. | |
| 2002/0062135 A1 | 5/2002 | Mazzocchi et al. | |
| 2002/0072765 A1 | 6/2002 | Mazzocchi et al. | |
| 2002/0077698 A1 | 6/2002 | Peredo | |
| 2002/0082525 A1 | 6/2002 | Oslund et al. | |
| 2002/0082613 A1 | 6/2002 | Hathaway et al. | |
| 2002/0095172 A1 | 7/2002 | Mazzocchi et al. | |
| 2002/0095173 A1 | 7/2002 | Mazzocchi et al. | |
| 2002/0143289 A1 * | 10/2002 | Ellis et al. | 604/22 |
| 2002/0161424 A1 | 10/2002 | Rapacki et al. | |
| 2002/0161432 A1 | 10/2002 | Mazzucco et al. | |
| 2002/0165606 A1 | 11/2002 | Wolf et al. | |
| 2002/0169377 A1 * | 11/2002 | Khairkhahan et al. | 600/433 |
| 2002/0173742 A1 | 11/2002 | Keren et al. | |
| 2002/0177894 A1 | 11/2002 | Acosta et al. | |
| 2002/0183826 A1 | 12/2002 | Dorn et al. | |
| 2002/0198563 A1 | 12/2002 | Gainor et al. | |
| 2003/0093072 A1 * | 5/2003 | Friedman | 606/41 |
| 2004/0044351 A1 | 3/2004 | Searle | |
| 2004/0087937 A1 * | 5/2004 | Eggers et al. | 606/41 |
| 2004/0093075 A1 | 5/2004 | Kuehne | |
| 2004/0102719 A1 | 5/2004 | Keith et al. | |
| 2004/0102797 A1 * | 5/2004 | Golden et al. | 606/153 |
| 2004/0111095 A1 | 6/2004 | Gordon et al. | |
| 2004/0133236 A1 | 7/2004 | Chanduszko | |
| 2004/0143292 A1 | 7/2004 | Marino et al. | |
| 2004/0162514 A1 | 8/2004 | Alferness et al. | |
| 2004/0176788 A1 | 9/2004 | Opolski | |
| 2004/0193261 A1 | 9/2004 | Berreklouw | |
| 2004/0206363 A1 | 10/2004 | Mccarthy et al. | |
| 2004/0220653 A1 | 11/2004 | Borg et al. | |
| 2004/0236308 A1 * | 11/2004 | Herweck et al. | 604/509 |
| 2004/0243143 A1 | 12/2004 | Corcoran et al. | |
| 2004/0267306 A1 | 12/2004 | Blaeser et al. | |
| 2005/0049692 A1 | 3/2005 | Numamoto et al. | |
| 2005/0065507 A1 * | 3/2005 | Hartley et al. | 606/41 |
| 2005/0065548 A1 | 3/2005 | Marino et al. | |
| 2005/0065589 A1 | 3/2005 | Schneider et al. | |
| 2005/0070934 A1 | 3/2005 | Tanaka et al. | |

(56) References Cited

U.S. PATENT DOCUMENTS

| | | |
|---|---|---|
| 2005/0075655 A1 | 4/2005 | Bumbalough et al. |
| 2005/0080400 A1 | 4/2005 | Corcoran et al. |
| 2005/0137609 A1* | 6/2005 | Guiraudon .......... 606/108 |
| 2005/0148925 A1 | 7/2005 | Rottenberg et al. |
| 2005/0165344 A1 | 7/2005 | Dobak, III |
| 2005/0187616 A1 | 8/2005 | Realyvasquez |
| 2005/0240205 A1* | 10/2005 | Berg et al. .......... 606/153 |
| 2005/0251063 A1* | 11/2005 | Basude .......... 600/564 |
| 2005/0267523 A1 | 12/2005 | Devellian et al. |
| 2005/0273075 A1* | 12/2005 | Krulevitch et al. .......... 604/509 |
| 2005/0288722 A1 | 12/2005 | Eigler et al. |
| 2006/0004434 A1 | 1/2006 | Forde et al. |
| 2006/0009715 A1 | 1/2006 | Khairkhahan et al. |
| 2006/0009800 A1 | 1/2006 | Christianson et al. |
| 2006/0122646 A1 | 6/2006 | Corcoran et al. |
| 2006/0122647 A1 | 6/2006 | Callaghan et al. |
| 2006/0136043 A1 | 6/2006 | Cully et al. |
| 2006/0155305 A1 | 7/2006 | Freudenthal et al. |
| 2006/0184088 A1* | 8/2006 | Van Bibber et al. .......... 604/8 |
| 2006/0241745 A1 | 10/2006 | Solem |
| 2006/0247680 A1 | 11/2006 | Amplatz et al. |
| 2006/0253184 A1 | 11/2006 | Amplatz |
| 2006/0276882 A1 | 12/2006 | Case et al. |
| 2007/0016250 A1 | 1/2007 | Blaeser et al. |
| 2007/0027528 A1 | 2/2007 | Agnew |
| 2007/0038295 A1 | 2/2007 | Case et al. |
| 2007/0043431 A1 | 2/2007 | Melsheimer |
| 2007/0088388 A1 | 4/2007 | Opolski et al. |
| 2007/0118207 A1 | 5/2007 | Amplatz et al. |
| 2007/0123934 A1 | 5/2007 | Whisenant et al. |
| 2007/0168019 A1 | 7/2007 | Amplatz et al. |
| 2007/0185513 A1 | 8/2007 | Woolfson et al. |
| 2007/0209957 A1 | 9/2007 | Glenn et al. |
| 2007/0225759 A1 | 9/2007 | Thommen et al. |
| 2007/0265658 A1 | 11/2007 | Nelson et al. |
| 2007/0270741 A1 | 11/2007 | Hassett et al. |
| 2007/0282157 A1 | 12/2007 | Rottenberg et al. |
| 2008/0015619 A1 | 1/2008 | Figulla et al. |
| 2008/0033425 A1 | 2/2008 | Davis et al. |
| 2008/0033543 A1 | 2/2008 | Gurskis et al. |
| 2008/0039804 A1 | 2/2008 | Edmiston et al. |
| 2008/0039922 A1 | 2/2008 | Miles et al. |
| 2008/0058940 A1 | 3/2008 | Wu et al. |
| 2008/0071135 A1 | 3/2008 | Shaknovich |
| 2008/0086168 A1 | 4/2008 | Cahill |
| 2008/0103508 A1 | 5/2008 | Karakurum |
| 2008/0119891 A1 | 5/2008 | Miles et al. |
| 2008/0125861 A1 | 5/2008 | Webler et al. |
| 2008/0154250 A1* | 6/2008 | Makower et al. .......... 606/10 |
| 2008/0154302 A1 | 6/2008 | Opolski et al. |
| 2008/0154351 A1 | 6/2008 | Leewood et al. |
| 2008/0172123 A1 | 7/2008 | Yadin |
| 2008/0183279 A1 | 7/2008 | Bailey et al. |
| 2008/0188888 A1 | 8/2008 | Adams et al. |
| 2008/0215008 A1 | 9/2008 | Nance et al. |
| 2008/0228264 A1 | 9/2008 | Li et al. |
| 2008/0249612 A1 | 10/2008 | Osborne et al. |
| 2008/0262592 A1 | 10/2008 | Jordan et al. |
| 2008/0269662 A1* | 10/2008 | Vassiliades et al. .......... 604/8 |
| 2008/0312679 A1 | 12/2008 | Hardert et al. |
| 2009/0018562 A1 | 1/2009 | Amplatz et al. |
| 2009/0025820 A1 | 1/2009 | Adams |
| 2009/0030495 A1 | 1/2009 | Koch |
| 2009/0062841 A1 | 3/2009 | Amplatz et al. |
| 2009/0082803 A1 | 3/2009 | Adams et al. |
| 2009/0099647 A1 | 4/2009 | Glimsdale et al. |
| 2009/0112050 A1 | 4/2009 | Farnan et al. |
| 2009/0112244 A1 | 4/2009 | Freudenthal |
| 2009/0131978 A1 | 5/2009 | Gainor et al. |
| 2009/0171386 A1 | 7/2009 | Amplatz et al. |
| 2009/0187214 A1 | 7/2009 | Amplatz et al. |
| 2009/0209855 A1 | 8/2009 | Drilling et al. |
| 2009/0210047 A1 | 8/2009 | Amplatz et al. |
| 2009/0210048 A1 | 8/2009 | Amplatz et al. |
| 2009/0234443 A1 | 9/2009 | Ottma et al. |
| 2009/0264991 A1 | 10/2009 | Paul, Jr. et al. |
| 2009/0270840 A1 | 10/2009 | Miles et al. |
| 2009/0270909 A1 | 10/2009 | Oslund et al. |
| 2010/0022940 A1 | 1/2010 | Thompson |
| 2010/0023046 A1 | 1/2010 | Heidner et al. |
| 2010/0023048 A1 | 1/2010 | Mach |
| 2010/0023121 A1 | 1/2010 | Evdokimov et al. |
| 2010/0030321 A1 | 2/2010 | Mach |
| 2010/0049307 A1 | 2/2010 | Ren |
| 2010/0057192 A1 | 3/2010 | Celermajer |
| 2010/0063578 A1 | 3/2010 | Ren et al. |
| 2010/0094335 A1 | 4/2010 | Gerberding et al. |
| 2010/0106235 A1 | 4/2010 | Kariniemi et al. |
| 2010/0121370 A1 | 5/2010 | Kariniemi |
| 2010/0131053 A1 | 5/2010 | Agnew |
| 2010/0179491 A1 | 7/2010 | Adams et al. |
| 2010/0211046 A1 | 8/2010 | Adams et al. |
| 2010/0234881 A1 | 9/2010 | Blaeser et al. |
| 2010/0249909 A1 | 9/2010 | McNamara et al. |
| 2010/0249910 A1 | 9/2010 | McNamara et al. |
| 2010/0256548 A1 | 10/2010 | McNamara et al. |
| 2010/0256753 A1 | 10/2010 | McNamara et al. |
| 2010/0298755 A1 | 11/2010 | McNamara et al. |
| 2010/0324588 A1 | 12/2010 | Miles et al. |
| 2011/0004239 A1 | 1/2011 | Russo et al. |
| 2011/0004296 A1 | 1/2011 | Lutter et al. |
| 2011/0022079 A1 | 1/2011 | Miles et al. |
| 2011/0071623 A1 | 3/2011 | Finch et al. |
| 2011/0071624 A1 | 3/2011 | Finch et al. |
| 2011/0093062 A1 | 4/2011 | Cartledge et al. |
| 2011/0106149 A1 | 5/2011 | Ryan et al. |
| 2011/0112633 A1 | 5/2011 | Devellian et al. |
| 2011/0130784 A1 | 6/2011 | Kusleika |
| 2011/0190874 A1 | 8/2011 | Celermajer et al. |
| 2011/0213364 A1 | 9/2011 | Davis et al. |
| 2011/0218477 A1 | 9/2011 | Keren et al. |
| 2011/0218478 A1 | 9/2011 | Keren et al. |
| 2011/0218479 A1 | 9/2011 | Rottenberg et al. |
| 2011/0218480 A1 | 9/2011 | Rottenberg et al. |
| 2011/0218481 A1 | 9/2011 | Rottenberg et al. |
| 2011/0257723 A1 | 10/2011 | Mcnamara |
| 2011/0270239 A1* | 11/2011 | Werneth .......... 606/33 |
| 2011/0283871 A1 | 11/2011 | Adams |
| 2011/0295182 A1 | 12/2011 | Finch et al. |
| 2011/0295183 A1 | 12/2011 | Finch et al. |
| 2011/0295362 A1 | 12/2011 | Finch et al. |
| 2011/0295366 A1 | 12/2011 | Finch et al. |
| 2011/0306916 A1 | 12/2011 | Nitzan et al. |
| 2011/0307000 A1 | 12/2011 | Amplatz et al. |
| 2012/0053686 A1 | 3/2012 | Mcnamara et al. |
| 2012/0130301 A1 | 5/2012 | Mcnamara et al. |
| 2012/0165928 A1* | 6/2012 | Nitzan et al. .......... 623/2.15 |
| 2012/0265296 A1 | 10/2012 | Mcnamara et al. |
| 2012/0289882 A1 | 11/2012 | Mcnamara et al. |
| 2012/0290062 A1 | 11/2012 | Mcnamara et al. |
| 2013/0178783 A1 | 7/2013 | McNamara et al. |
| 2013/0178784 A1 | 7/2013 | McNamara et al. |
| 2013/0184633 A1 | 7/2013 | McNamara et al. |
| 2013/0184634 A1 | 7/2013 | McNamara et al. |
| 2013/0231737 A1 | 9/2013 | McNamara et al. |
| 2013/0267885 A1 | 10/2013 | Celermajer et al. |

FOREIGN PATENT DOCUMENTS

| | | |
|---|---|---|
| CN | 102908213 A | 2/2013 |
| EP | 1470785 | 10/2004 |
| EP | 2528646 A2 | 12/2012 |
| EP | 2537490 A1 | 12/2012 |
| WO | WO-9527448 A1 | 10/1995 |
| WO | WO-2008055301 A1 | 5/2008 |
| WO | WO-2008058940 A1 | 5/2008 |
| WO | 2010111666 A1 | 9/2010 |
| WO | WO-2010128501 A1 | 11/2010 |
| WO | WO-2010129089 A2 | 11/2010 |
| WO | WO-2011093941 A2 | 8/2011 |
| WO | WO-2011094521 A2 | 8/2011 |
| WO | WO-2011093941 A3 | 10/2011 |
| WO | WO-2011093941 A4 | 12/2011 |
| WO | WO-2011094521 A3 | 12/2011 |

(56) References Cited

FOREIGN PATENT DOCUMENTS

| WO | WO-2012071075 A1 | 5/2012 |
|---|---|---|
| WO | WO-2012109557 A2 | 8/2012 |
| WO | 2012109557 A3 | 1/2013 |
| WO | 2013096965 A1 | 6/2013 |

OTHER PUBLICATIONS

European Application Serial No. 10772411.4, Office Action mailed Nov. 29, 2012, 3 pages.
European Application Serial No. EP12180631.9, European Search Report mailed Nov. 19, 2012, 5 pages.
International Application Serial No. PCT/AU2007/01704, Written Opinion mailed Jan. 16, 2008, 5.
Ad et al., "A one way valved atrial septal patch: A new surgical technique and its clinical application", The Journal of Thoracic and Cardiovascular Surgery, vol. 111, No. 4, Apr. 1996, 841-848.
Althoff et al., "Long-Term follow up of a fenestrated amplatzer atrial septal occluder in pulmonary arterial hypertension", American College of Chest Physicians 2008, Chest, vol. 133, No. 1, Jan. 2008, 5.
Atz et al., "Preoperative Management of Pulmonary Venous Hypertension in Hypoplastic Left Heart Syndrome With Restrictive Atrial Septal Defect", The American Journal of Cardiology, vol. 83, Apr. 15, 1999, 1224-1228.
Bailey, Steven R., "Nanotechnology in prosthetic heart valves", EuroPCR 2005, May 24-27, 2005, 31.
Bolling, Steven F., "Direct Flow medical-my valve is better", Direct Flow medical Inc., Apr. 23, 2009, 21.
Caselli, Joseph S., "No! valve replacement: patient prosthetic mismatch rarely occurs", Texas Heart Institute, Apr. 25, 2009, 75.
Cheatham, John P., "Intervention in the critically ill neonate and infant with hypoplastic left heart syndrome and intact atrial septum", Journal of Interventional Cardiology, vol. 14, No. 3, 2001, 357-366.
Design News, "Low Power Piezo Motion", http://www.designnews.com/document.asp?doc_id=229053&dfpPParams&dfpPParams=ht_13,aid_229053&dfpLayout=article, May 14, 2010, 3.
Gaudiani et al., "A philosophical approach to mitral valve repair", Dallas-Leipzig International Valve Congress, Apr. 24, 2009, 28.
Hijazi, Ziyad M., "Valve Implantation", Pediatric & Adult Interventional Therapies for Congenital and Valvular Heart. Disease, Jul. 22-25, 2007, 36.
Larios et al., "The Use of an Artificial Foraminal Valve Prosthesis in the Closure of Interatrial and Interventricular Septal Defects", American Ccollege of Chest Physicains, Dis. Chest. 1959, vol. 36, Dec. 1959, 12.
Leon, Martin B., "Transcatheter Aortic Valve Therapy: Summary Thoughts", Transcatheter Valve Therapies, Jun. 24-26, 2009, 19.
McMahon, Jim, "Piezo motors and actuators: Streamlining medical device performance", DesignFax News, Mar. 23, 2010, 5.
Merchant et al., "Advances in Arrhythmia and Electrophysiology; Implantable Sensors for Heart Failure", Circ. Arrhythm. Electrophysiol., vol. 3, Dec. 2010, 657-667.
Moses, Jeffrey W., "The Good, the Bad and the ugly of transcatheter AVR", Jul. 10, 2009, 28.
O'Loughlin et al., "Insertion of a Fenestrated Amplatzer Atrial Sestosotomy Device for Severe Pulmonary Hypertension", Heart ,Lung and Circulation, vol. 15, 2006, 275-277.
Park et al., "Blade atrial septostomy: collaborative study", Circulation, Journal of the American Heart Association, vol. 66, No. 2, Aug. 1982.

International Application Serial No. PCT/AU2007/001704, International Search Report mailed Jan. 16, 2008, 4.
International Application U.S. Appl. No. PCT/AU2007/01704, International Preliminary Report on Patentability mailed Aug. 22, 2008, 5.
International Application Serial No. PCT/US2010/026574, International Preliminary Report on Patentability mailed Nov. 10, 2011, 7.
International Application Serial No. PCT/US2010/026574, International Search Report and Written Opinion mailed Nov. 19, 2010, 9.
International Application Serial No. PCT/US2010/58110, International Search Report and Written Opinion mailed Aug. 26, 2011, 14.
International Application Serial No. PCT/US10/58110, International Preliminary Report on Patentability mailed Nov. 27, 2012, 11 pages.
International Application Serial No. PCT/US2011/041841, International Search Report mailed Feb. 9, 2012, 12.
International Application Serial No. PCT/US2011/22895, International Search Report & Written Opinion mailed Oct. 24, 2011, 11.
Pedra et al., "Stent Implantation to Create Interatrial Communications in Patients With Complex Congenital Heart Disease", Catheterization and Cardiovascular Interventions 47, Jan. 27, 1999, 310-313.
Perry et al., "Creation and Maintenance of an Adequate Interatrial Communicationin left Atrioventricular Valve Atresia or Stenosis", The American Journal of Cardiology, vol. 58, Sep. 15, 1986, 622-626.
Philips et al., "Ventriculofemoroatrial shunt: a viable alternative for the treatment of hydrocephalus", J. Neurosurg., vol. 86, Jun. 1997, 1063-1066.
Physik Instrumente, "Piezo for Motion Control in Medical Design and Drug Research", Physik Instrumente (PI) GmbH & Co. KG, Nov. 21, 2010, 22.
RPI Newswire, "Implantable, Wireless Sensors Share Secrets of Healing Tissues", RPI Newswire, http://news.rpi.edu/update.do, Feb. 21, 2012, 1.
Sommer et al., "Transcatheter Creation of Atrial Septal Defect and Fontan Fenestration with "Butterfly" Stent Technique", Supplement to Journal of the American College of Cardiology, V. 33, No. 2, Supplement A, Feb. 1999, 3.
Stone, Gregg W., "Transcatheter devices for mitral valve repair surveying the landscape", Columbia University Medical Center, Jul. 10, 2009, 48.
Stormer et al., "Comparative Study of in vitro Flow Characteristics between a Human Aortic Valve and a Designed Aortic Valve and Six Corresponding Types of Prosthetic Heart Valves", Eur. Surg. Res., vol. 8, No. 2, 1976, 117-131.
Watterson et al., "Very Small Pulmonary Arteries: Central End-to-Side Shunt", Ann. Thorac. Surg., vol. 52, No. 5, Nov. 1991, 1132-1137.
Weber, Ralph, "Piezo Motor Based Medical Devices", Medical Design Technology, Apr. 2, 2009, 5.
PCT/US2012/071588, International Application Serial No. PCT/US2012/071588, International Search Report and Written Opinion mailed Apr. 19, 2013, DC Devices, Inc., 19 pages.
International Search Report and Written Opinion, PCT/US12/024680, mailed Oct. 23, 2012, 11 pages.
PCT/US12/024680, International Application Serial No. PCT/US12/024680, International Preliminary Report on Patentability and Written Opinion mailed Aug. 22, 2013, DC Devices, Inc, 7 pages.
PCT/US2011/041841, International Application Serial No. PCT /US2011/041841, International Preliminary Report on Patentability and Written Opinion mailed Jun. 6, 2013, DC Devices, Inc. et al, 8 pages.

\* cited by examiner

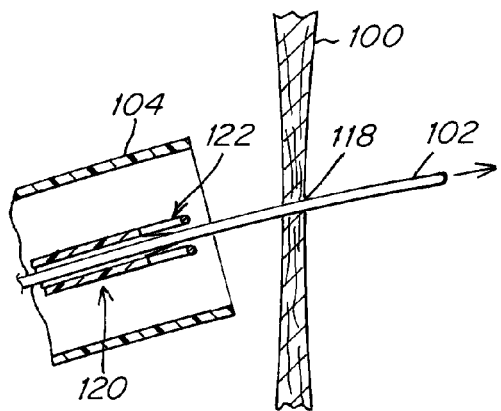
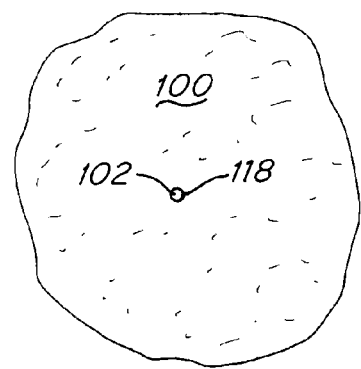
Fig. 6A Fig. 6B
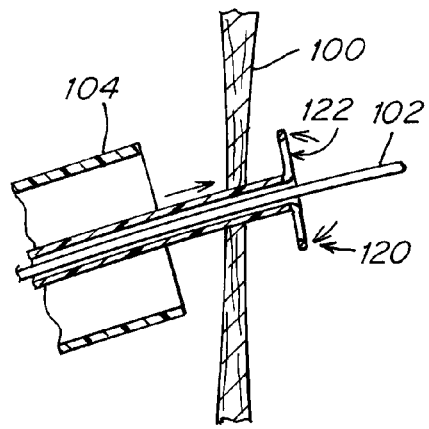
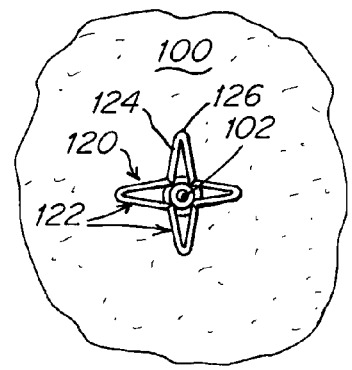
Fig. 6C Fig. 6D

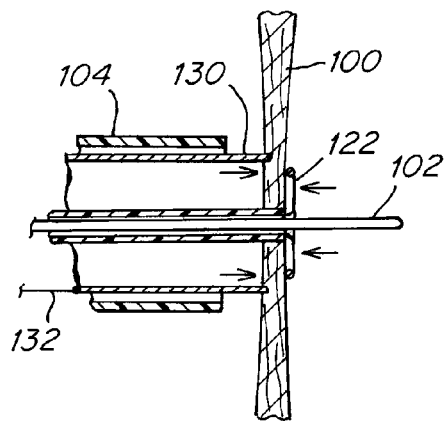 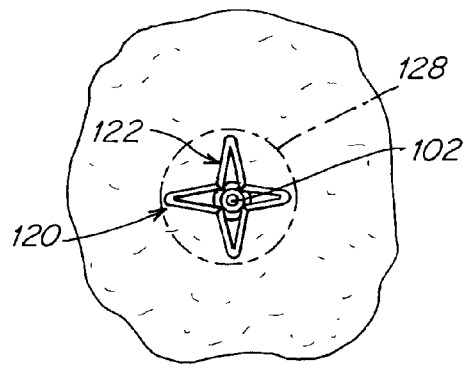
Fig. 6E         Fig. 6F
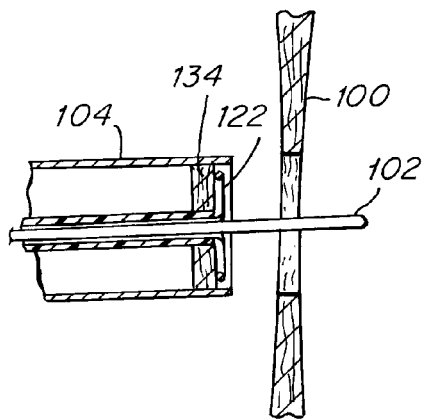 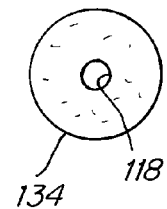
Fig. 6G         Fig. 6H

APPARATUS AND METHODS TO CREATE AND MAINTAIN AN INTRA-ATRIAL PRESSURE RELIEF OPENING

CLAIM TO PRIORITY

The present application incorporates by reference in their entirety the following prior patent applications: U.S. Prov. Appl. No. 61/441,546, filed Feb. 10, 2011, U.S. patent application Ser. No. 13/290,295, filed Nov. 7, 2011, now U.S. Pat. No. 8,460,372, U.S. patent application Ser. No. 12/954,541, filed Nov. 24, 2010, U.S. application Ser. No. 12/719,843, filed Mar. 8, 2010, now U.S. Pat. No. 8,157,860, U.S. Provisional Application Ser. No. 61/299,559, filed Jan. 29, 2010, U.S. patent application Ser. No. 12/447,617, filed Apr. 28, 2009, international application PCT/AU2007/001704 filed Nov. 7, 2007, Australian Patent Application No. AU 2006906202 filed Nov. 7, 2006, and U.S. Provisional Application Ser. No. 61/240,085 filed Sep. 4, 2009.

FIELD

The present disclosure relates to a method and a device for treating heart failure, more particularly to a method and a device for treating heart failure by reducing elevated blood pressure in a heart chamber by creating an intra-atrial pressure relief opening. Additionally, the present disclosure relates to a method and a device for maintaining or prolonging the patency of an intra-atrial pressure relief opening.

BACKGROUND

Heart failure is a condition effecting millions of people worldwide. Heart failure includes failure of either the left side of the heart, the right side of the heart, or both. Left heart failure can lead to elevated pulmonary venous pressure, which may cause respiratory problems, including shortness of breath and exercise intolerance. Left heart failure may be ascribed to a number of causes, including valve disease, systolic failure of the left ventricle, and diastolic failure of the left ventricle. The adverse clinical result of each of these conditions is similar; the heart failure leads to elevated pressure in the left atrium and elevated pressure in the pulmonary veins, impeding proper flow of oxygenated blood through the blood supply. Therefore, there exists a need to treat the adverse effects of elevated pulmonary venous pressure on the body.

Heart failure has been further classified as either systolic heart failure or diastolic heart failure. Diastolic heart failure refers to heart failure that is present without the presence of major valve disease even while the systolic function of the left ventricle is preserved. More generally, diastolic heart failure is failure of the ventricle to adequately relax and expand in order to fill with blood, causing a decrease in the stroke volume of the heart. Presently, there exist very few treatment options for patients suffering from diastolic heart failure. Therefore there exists a need for methods and devices for treating elevated pulmonary venous pressures caused by diastolic heart failure.

A few techniques have been disclosed for reducing elevated pulmonary venous pressure; however these techniques all suffer from critical deficiencies. For example, U.S. Published patent application Ser. No. 09/839,643 by Keren et al discloses the use of a complex an intra-atrial pressure relief shunt including a stented valve. This approach suffers from several deficiencies. First, the proposed treatment requires the implantation of a complex implant device, which increases the risk of various clinical complications and adverse events. The implant resides partially in both the left atrium and right atrium, and poses a risk of generating thrombus and releasing emboli into the left or right circulation.

Releasing emboli into the left circulation could lead to a myocardial infarction or stroke. Additionally, the valve apparatus requires moving parts, which increases the risks associated with long term implant material fatigue and device fracture. A device fracture could in turn lead to embolization of all or part of the implant. Additionally, the valve incorporated into the shunt has the potential to fail acutely, possibly leading to a rapid increase in the load on the left heart. The patient could conceivably experience a significant acute circulatory pressure overload caused by sudden closure of the therapeutic shunt, potentially leading to severe complications. Therefore, there still exists a need for a simple and effective means of treating elevated pulmonary venous pressures caused by heart failure.

SUMMARY

In general, the present disclosure relates to a method and a device for treatment of heart failure by reducing both left atrial and pulmonary venous pressure which includes the creation of an intra-atrial pressure relief opening in the atrial septum. Furthermore, the method and the device disclosed herein provide treatment to the tissue near the intra-atrial pressure relief opening in order to maintain the long term patency of the opening.

The method and the device are particularly useful for treating the symptoms of left heart failure, and in particular diastolic heart failure, by reducing the pressure in the left atrium and pulmonary veins.

The present disclosure relates to a catheter device for treating heart failure. The catheter device includes an outer sheath having at least one lumen. The device also includes a penetrator for penetrating an atrial septum between a first high pressure chamber and a second low pressure chamber in a heart of a patient by creating an opening in the atrial septum and a dilator for enlarging the opening to a second substantially larger opening, thereby creating an intra-atrial pressure relief opening in the atrial septum. The device also includes a mechanism suitable for treating the atrial septum substantially surrounding the intra-atrial pressure relief opening in order to avoid natural healing of the second substantially larger opening in the septum. The second substantially larger opening is large enough to allow blood flow through the intra-atrial pressure relief opening from the first high pressure chamber to the second low pressure chamber. This reduces the atrial pressure and pulmonary venous pressure without implanting a mechanical device in the atrial septum.

The present disclosure also describes a method for normalizing elevated blood pressure in a heart chamber. The method includes steps of penetrating an atrial septum present between a first high pressure chamber and a second low pressure chamber of a heart to create a first opening in the atrial septum; dilating the first opening to a second substantially larger opening of a desired size to create an intra-atrial pressure relief opening; delivering at least one treatment to the atrial septum surrounding the intra-atrial pressure relief opening, wherein the second substantially larger opening is made large enough to allow blood flow through the intra-atrial pressure relief opening from the first high pressure chamber to the second low pressure chamber, thereby reducing the atrial pressure and pulmonary venous pressure.

Another method according to the present disclosure is a method for normalizing elevated blood pressure in a heart chamber of a patient. The method includes steps of penetrating an atrial septum between a first high pressure chamber and a second low pressure chamber of a heart to create a first opening in the atrial septum. The method also includes a step of dilating the first opening to a second substantially larger opening of a desired size to create an intra-atrial pressure relief opening, extracting tissue separated from the atrial septum of the patient and delivering at least one treatment to the atrial septum surrounding the intra-atrial pressure relief opening, wherein the second substantially larger opening is made large enough to allow blood flow through the intra-atrial pressure relief opening from the first high pressure chamber to the second low pressure chamber without implanting a stent or a valve in the atrial septum.

In one of the embodiments of the present disclosure, the intra-atrial pressure relief opening is created in the atrial septum in the region of the septum generally near the fossa ovalis. The intra-atrial pressure relief opening is configured to allow a therapeutic amount of communication of blood between the left atrium and the right atrium, in order to reduce the negative clinical outcomes associated with elevated left atrial and pulmonary venous pressure. The said method delays the natural healing response of the septum tissues surrounding the intra-atrial pressure relief opening which would otherwise act to occlude the opening.

In exemplary embodiments of the present disclosure, dilation of the first diameter opening to a second substantially larger diameter opening to create an intra-atrial pressure relief opening is done by a conical distal tip of dilation catheter.

In some embodiments of the present disclosure, dilation of the first diameter opening to a second substantially larger diameter opening to create an intra-atrial pressure relief opening is done using a balloon catheter.

In some of embodiments of the present disclosure, the intra-atrial pressure relief opening may be treated with a treatment means, in order to treat the tissue in a manner that disrupts, slows, or reduces the body's ability to heal and occlude the therapeutic an intra-atrial pressure relief opening. The treatment means may include an energy delivery means, such as a means for delivering RF energy, ultrasound energy, laser energy, visible light energy or UV light energy to the tissue in the vicinity of the intra-atrial pressure relief opening.

In additional embodiments, the treatment means may include a means for delivering or removing thermal energy from the tissue, such as heating the tissue with steam, burning the tissue with heat generated by other means, or freezing the tissue with a cryogenically cooled heat transfer medium.

In still other embodiments the treatment means includes a means for physically or mechanically abrading the tissue in the vicinity of the intra-atrial pressure relief opening, thereby inducing the formation of a thickened scar tissue in the vicinity of the opening, and slowing the healing response of the body.

In other embodiments the treatment means includes a means for fixing or gluing the tissue by secreting a fixative or adhesive to the tissue in the vicinity of the intra-atrial pressure relief opening. In still other embodiments the treatment means may includes a catheter designed to ablate the tissue in the vicinity of the intra-atrial pressure relief opening by exposing the tissue to alcohol, thereby limiting the body's ability to heal and subsequently occlude the intra-atrial pressure relief opening.

In additional embodiments of the present disclosure, an intra-atrial pressure relief opening is created by piercing the atrial septum with a wire or other suitable device. A specially designed balloon catheter is then introduced into the newly created first diameter opening in the atrial septum. The balloon features a coating which incorporates at least one anti-proliferative drug or immunosuppressant drug. The balloon is then inflated, thereby simultaneously dilating the opening, creating an intra-atrial pressure relief opening, and depositing a coating of the drug onto the tissue in the vicinity of the intra-atrial pressure relief opening. In this way the normal healing responses of the body is disrupted and the long term patency of the intra-atrial pressure relief opening is increased.

In another embodiment, a medication is applied to an inner surface of tissue within a patient. In this method, a balloon is prepared with a medication on an outer surface of the balloon. In one variant, the medication is place in an absorbent pad on the outer surface of the balloon. The balloon is deployed within the patient using a sheath, and the balloon is inflated to apply the medication in an inner surface of tissue within the patient. In one embodiment, the inner surface is an opening within an atrial septum. In one embodiment the medication is sirolimus, paclitaxel, zotarolimus, everolimus, silver nitrate, pyrimidine, methotrexate, azathioprine, dactinmycin, formalin, formaldehyde and ethanol.

The tools, apparatuses and methods disclosed herein provide many advantages. One advantage is reducing heart failure by reducing high pressure within a chamber of the heart and also by reducing pulmonary venous pressure. The intra-atrial pressure relief openings disclosed herein do not leave behind any complex, expensive or potentially hazardous implant. The treatments described herein also prolong or maintain the patency of an intra-atrial relief opening by preventing or substantially delaying natural healing processes of intra-atrial septum tissues present in the vicinity of the intra-atrial pressure relief opening. In addition, the methods and techniques described herein create a fail-safe intra-atrial pressure relief opening that is incapable of failing acutely, and which can become occluded only over an extended or clinically significant period of time. The devices and methods described herein create an intra-atrial pressure relief opening to allow blood to flow from the left atrium to the right atrium, thereby reducing pressure in the left atrium and in the pulmonary veins. The embodiments described herein accomplish this by treating tissue in the vicinity of the opening to prevent or substantially slow the healing response which would normally act to close the intra-atrial pressure relief opening.

The foregoing and other features and advantages of the present disclosure will become further apparent from the following detailed description of the presently preferred embodiments, read in conjunction with the accompanying drawings, which are not to scale. The detailed description and drawings are merely illustrative of the disclosure, rather than limiting the scope of the disclosure being defined by the appended claims and equivalents thereof. Specific details are disclosed which would allow one with ordinary skill in the art to make and use the inventive devices and practice the inventive methods. It should be understood that various substitutions and additions can be made by those with ordinary skill in the art while still falling within the inventive features disclosed herein.

BRIEF DESCRIPTION OF THE DRAWINGS

FIGS. 6A-6D depict partial cross-sectional views of a technique for making an additional opening in the patient's septal wall.

FIGS. 6E-6H depict additional partial cross-sectional views of an alternate way of making an initial opening in the patient's septal wall.

DETAILED DESCRIPTION

Figure 1:
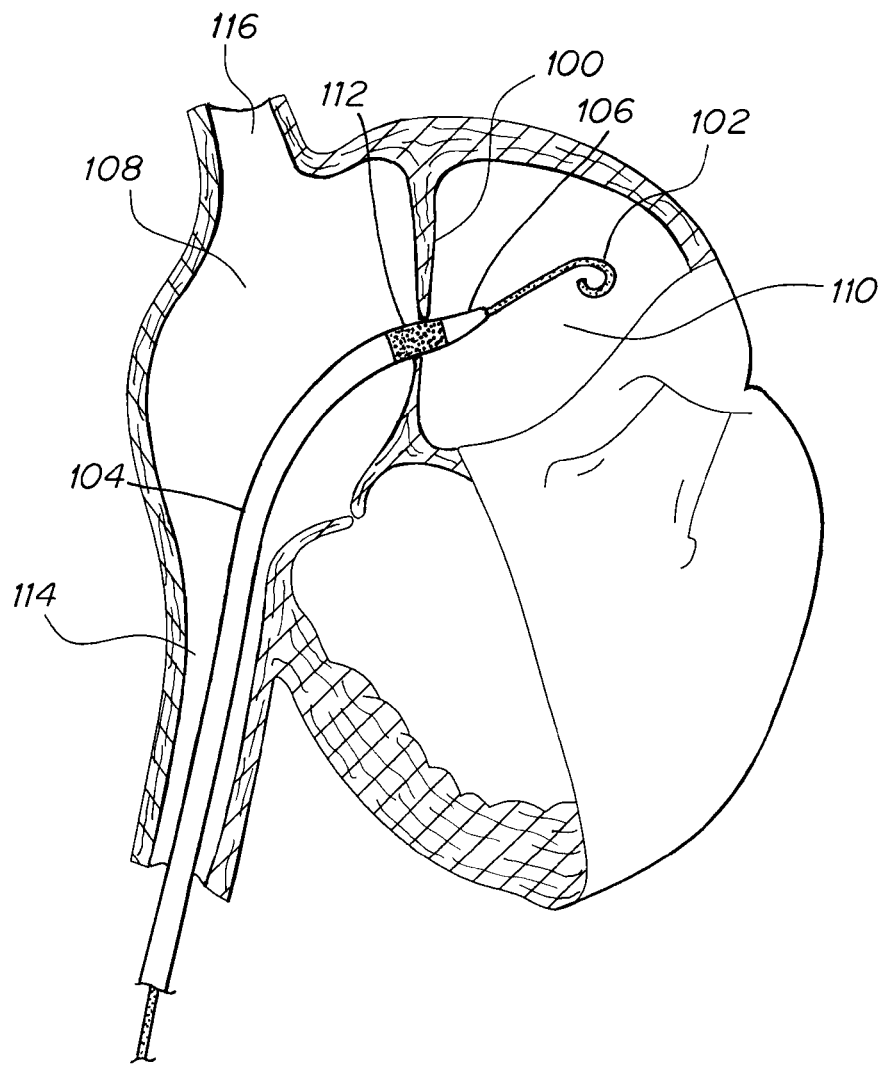
FIG. 1 is a cross sectional side view of the device implanted in a human heart.

Referring to FIG. 1, an embodiment is depicted for treating heart failure. FIG. 1 shows an atrial septum 100 which has been penetrated by a wire 102 thereby creating a first diameter opening and further dilated to second substantially larger diameter opening with aid of a dilation means 106. The dilation means is a conical distal tip 106 of a dilation catheter 104 which is configured to allow for the user to dilate the first a diameter opening created by the wire 102. The wire 102 and dilation catheter 104 extend from the right atrium 108 and into the left atrium 110. The dilation catheter 104 is equipped with a treatment means 112 for delivering energy to the septum tissues in the vicinity of the first diameter opening being enlarged by the dilation means 106. In FIG. 1 the means for delivering energy is depicted as a stipple-shaded region on the dilation catheter 104. The treatment means 112 for delivering energy may be used to ablate the tissue near the second larger diameter opening created by the dilation means 106, in order to improve the long term patency of the intra-atrial pressure relief opening created by the wire 102 and dilation means 106.

The crossing wire 102 of FIG. 1 may be any suitably stiff wire currently available for catheter procedures, or it may be custom made for the procedure. The wire 102 may include a sharpened tip in order to more easily penetrate the septum 100. The wire 102 may be made of stainless steel, nitinol, or any other suitable material. After crossing the septum 100 the wire 102 may be withdrawn from the body, or may be left behind in order to facilitate the advancement of further devices and catheters into the body. In addition the wire 102 may feature a curved distal section in order to prevent the user from accidentally puncturing the wall of the left atrium 110. In one embodiment, the guide wire 102 is a 0.9 mm (0.035") J-curve nitinol wire. In another embodiment, the guide wire 102 may be similar to the wires used in treating total coronary occlusions. The design, manufacture, and use of guide wires for penetrating tissue and lesions are well known in the art.

The dilation catheter 104 of FIG. 1 may be manufactured in a number of ways, and may be made of any suitable biocompatible material. A simple dilation catheter 104 might be made from LDPE, HDPE, or FEP and may feature a heat formed or over-molded conical tip. Another suitable dilation catheter 104 construction might include a PEBAX or nylon braided shaft with a specially designed conical cap 106. The dilation catheter features a generally circular cross-section, however ridges or texturing may be employed in order to more efficiently dilate the septum by creating localized stress-concentration on the tissue near the ridges. In addition, the distal conical section 106 of the dilation catheter 104 may incorporate a number of cutting features, such as small metallic blades, or sharpened plastic protrusions, in order more effectively dilate the atrial septum 100. The outer diameter (OD) of the dilation catheter 104 is designed to create an opening in the septum 100 that is large enough to allow enough blood to flow through the opening to substantially reduce the pulmonary vein and left atrial blood pressure. In some embodiments, the outer diameter of the dilation catheter 104 is roughly between 3 mm and 5 mm. The dilation catheter 104 may be configured to be advanced over a wire 102, and as such it may have at least one wire lumen. Additional lumens might be used to allow for additional functionality, including lumens for secondary treatment devices and for injection of biocompatible dye. Furthermore, the dilator may include a stopping feature to prevent the user from advancing the dilation catheter so far into the left atrium 110 that the energy delivering means 112 is no longer in contact with the tissue of the intra-atrial septum 100.

Still referring to FIG. 1, the dilation catheter extends from an access point in the lower veins, and extends into the right atrium 108 through the inferior vena cava 114. In alternative embodiments, the dilation catheter 104 may access the atrial septum 100 by other means, including from the jugular vein and through the superior vena cava 116. In addition, access to the atrial septum 100 may be provided by other means, including through minimally invasive surgery, and through other major vessels in the body.

Figure 2A:
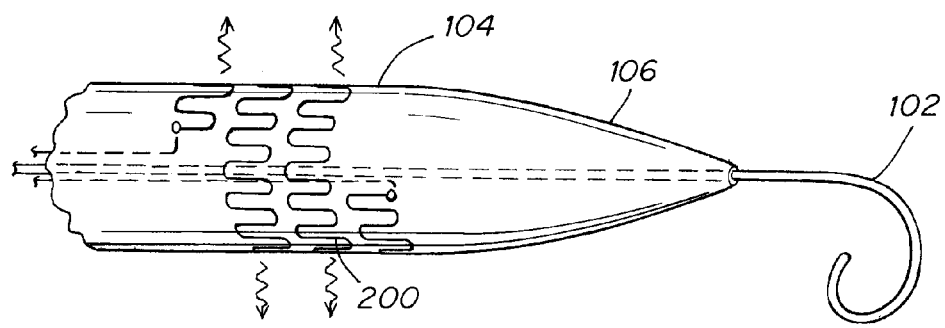
FIG. 2A is a side view of one embodiment depicting a catheter equipped with thin wire electrode as a means for delivering energy.

Referring now to FIGS. 2A to 2F, a series of exemplary energy delivering means are depicted. FIG. 2A shows a crossing wire 102 extending from a dilation catheter 104, featuring a conical distal tip 106. A thin wire electrode 200 is depicted spiraling around the shaft of the dilation catheter 104 just proximal to the conical tip 102. The path of the electrode 200 is tortuous, thereby maximizing the contact of the electrode 200 with the tissue. The electrode 200 is connected by a suitable means to an external power source, such as a DC power supply. When the power source pushes current across the electrode 200 the wire heats up due to the electrical resistance of the wire. The electrode 200 is electrically insulated from the body in order to prevent an adverse reaction to the current or a short circuit through the body. By carefully controlling the power being sent through the electrode 200 the surface temperature on the catheter shaft can be controlled. The electrical circuit may include a means for measuring or monitoring the temperature, and may also include an emergency circuit breaker, which could break the circuit if the temperature becomes too high. The heat energy is transferred from the dilator through to the tissue in order to ablate or otherwise damage the tissue surrounding the intra-atrial pressure relief opening. By ablating the tissue in the vicinity of the intra-atrial pressure relief opening the healing process is impeded and the patency of the intra-atrial pressure relief opening over time is improved.

Figure 2B:
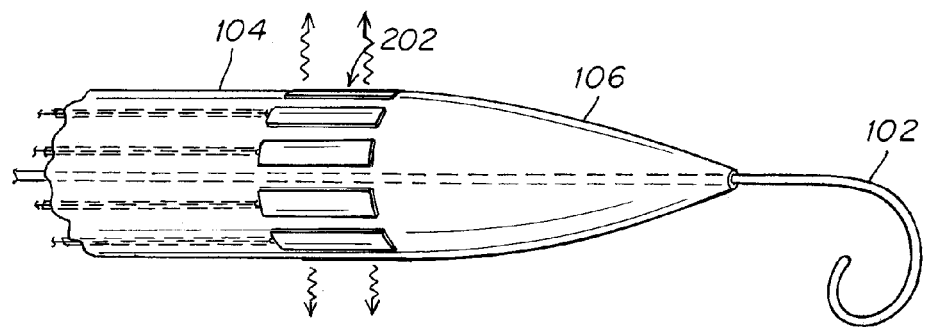
FIG. 2B is a side view of an embodiment depicting a catheter equipped with series of radio frequency electrodes as a means for delivering energy

Referring now to FIG. 2B, a dilation catheter 104 which features an elongate shaft and a conical tip 106 is depicted. A series of radio frequency (RF) electrodes 202 are exposed on the surface of the shaft, just proximal to the conical tip 106. The electrodes 202 are designed to carry monopolar radio frequency energy and to transfer the energy to the tissue. The RF energy may be supplied by a suitable RF generator, the likes of which are available to hospitals and are often available in catheter labs. The electrodes may be connected to the RF generator by means of an insulated conduction wire which runs or wires which run through the length of the catheter. A grounding pad may be attached to the patient's anatomy in order to represent a safe means for dissipating the electrical current after the tissue has been significantly ablated. The RF electrode array 202 therefore represents a means for delivering energy to the tissue surrounding the intra-atrial pressure relief opening in order to ablate the tissue.

Figure 2C:
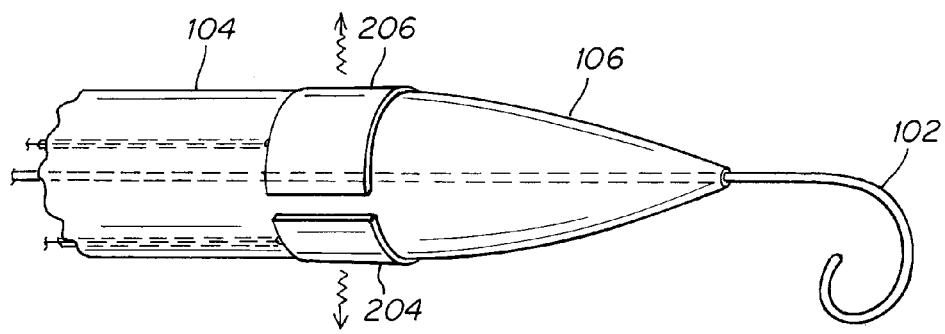
FIG. 2C is a side view of an embodiment depicting a catheter with two semi-circular electrodes designed to carry bi-polar radio frequency energy.

Referring now to FIG. 2C, a dilation catheter 104 which features an elongate shaft and a conical tip 106 is depicted. Two semi-circular radio-frequency electrodes 204 206 are shown. The electrodes 204, 206 are designed to carry bi-polar radio frequency energy and to transfer the energy to the tissue. For example, RF electrode 206 might represent a return electrode, where the radio-frequency energy might travel from electrode 204, through the tissue surrounding the dilation catheter 104, and complete the circuit by conduction of the RF electrode 206. The electrodes 204, 206 may be connected to an external RF generator in much the same way as the embodiment depicted in FIG. 2B. The use of RF energy to treat tissue is known in the art. For example, RF energy is employed in electrophysiology procedures for treating atrial fibrillation.

Figure 2D:
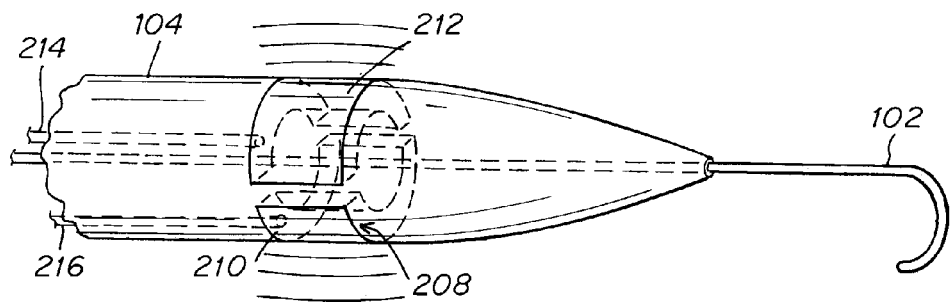
FIG. 2D is a side view of an embodiment depicting a catheter equipped with piezoelectric ultrasound transducers arrays as a means for delivering energy.

Referring now to FIG. 2D, a dilation catheter 104 is depicted with an energy delivering means 208 for treating tissue. The energy delivering means of FIG. 2D may be represented by two arrays of piezoelectric ultrasound transducers 210, 212. As required, additional arrays of piezoelectric ultrasound transducers may be used, for example, four such arrays may be spaced around the circumference of the dilation catheter 104. The ultrasound transducers 210, 212 are configured to emit high frequency focused ultrasonic energy when an appropriately phased alternating current is supplied to the transducers. This may be accomplished by connecting each transducer array to an electrical conduit 214, 216, which in turn is connected to an external power supply. The electrical conduits 214, 216 may include a plurality of individually insulated conductive wires. Each wire is configured to deliver an alternating current to a different section of the transducer array. The electrical current in each wire is carefully controlled by the external power supply such that the ultrasonic energy emitted across the array is appropriately phased in order to direct the overall signal to a focused region of tissue surrounding the dilation catheter 104.

Still referring to FIG. 2D, the phased transducer array works by a means well known in the art involving the use of waveform interference. The high intensity focused ultrasound emitted by the dilation catheter 104 in this way generates significant heat at the focal point of the ultrasound array. The array may be shaped to emit this focused ultrasound in a roughly circular pattern around the circumference of the shaft, thereby ablating the tissue in the vicinity of the dilation catheter 104. In this way the ultrasound array represents a means of treating the tissue in order to slow or prevent the natural healing process of the body.

Figure 2E:
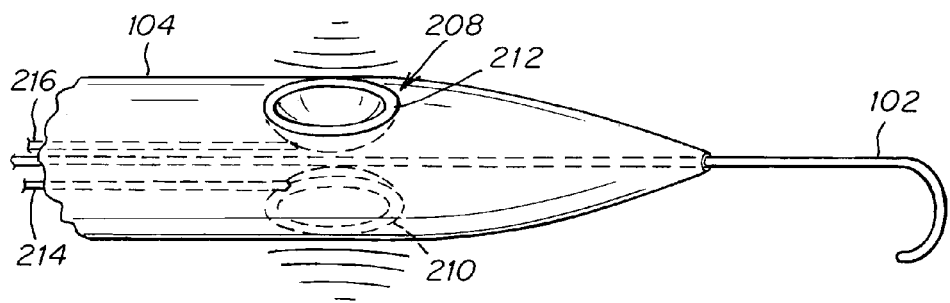
FIG. 2E is a side view of an embodiment depicting a catheter equipped with concave-shaped piezoelectric ultrasound transducers arrays as a means for delivering energy.

Referring now to FIG. 2E, a dilation catheter 104 which may be used to create an intra-atrial pressure relief opening is depicted with an energy treating means 208 for treating tissue. The energy delivering means is represented by two or more arrays of piezoelectric ultrasound transducers 210,212. Although two transducer arrays 210,212 are shown, however any number of such arrays may be employed to produce a similar effect. In contrast to FIG. 2D the transducer arrays of FIG. 2E are shaped like a concave lens, and this allows the transducer to naturally emit focused ultrasonic energy. The transducer arrays of FIG. 2E therefore emit focused ultrasonic energy without the need for separating elements of array into different phases. The transducer arrays are electrically connected to electrical conduits 214, 216, which are in turn connected to an external power supply. In this way alternating current can be generated by the power supply and eventually supplied to the ultrasound arrays 210, 212 by the electrical conduits 214, 216. The focused ultrasonic energy that is emitted heats up the tissue near the focal point of the array. In this way the ultrasonic array 210, 212 of FIG. 2E represents a means for damaging or ablating tissue in order to prevent or delay the natural healing process of the body, which would otherwise cause the intra-atrial pressure relief opening to close over time.

Figure 2F:
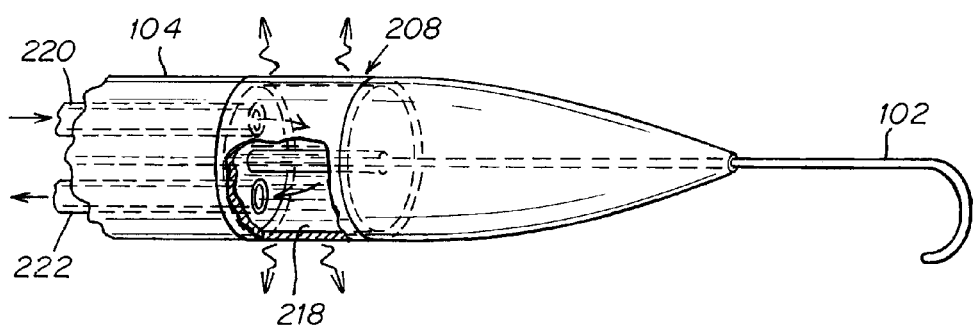
FIG. 2F is a side view of an embodiment depicting a catheter with annular cavity carrying a heat transfer fluid for delivering energy.

Referring now to FIG. 2F, a dilation catheter 104 which may be used to create a delivering means 208 for treating tissue surrounding the intra-atrial pressure relief opening. The energy delivering means is represented by an annular cavity 218 located inside the dilation catheter 104. The annular cavity 218 is connected to an inlet lumen 220 and an outlet lumen 222. A heat transfer fluid is pumped through the inlet lumen 220 and into the annular cavity 218, where it transfers or absorbs heat energy from the surroundings. The fluid is then pumped out the outlet lumen 222. In this way the heat transfer fluid is circulated throughout the annular cavity 218 of the dilation catheter 104. The heat transfer fluid may be any number of fluids, including very cold or very hot saline or water, steam, or a cryogenic fluid. In addition, nearly any suitable fluid or gas may be pumped at an appropriate temperature to treat the tissue. In some embodiments, the heat transfer fluid is saline and is pumped through the dilation catheter at 55-65 degrees Celsius. In other embodiments, the saline is pumped through the catheter at roughly negative 10 degrees Celsius.

The annular cavity 218 of the dilation catheter 104 depicted in FIG. 2F may be surrounded by a material with especially high heat conductance, such as stainless steel or other metals. In this way pumping either a hot or cold fluid through the annular cavity 218 can chill or heat the tissue surrounding the dilation catheter 104 in order to ablate or otherwise damage the tissue. Therefore, the dilation catheter 104 with a cavity 218 for circulating a heat transfer fluid represents a means of treating the tissue near the intra-atrial pressure relief opening in order to slow or prevent the natural healing process of the body.

The energy delivery means depicted in FIGS. 2A to 2F are not intended to be an exhaustive list of the various energy delivery means for treating the tissue. In addition to the depicted energy delivery means, a variety of other mechanisms for delivering energy may be used. In other embodiments, for example, high intensity unfocused light may be channeled through an optical fiber in the catheter and directed towards the tissue surrounding the intra-atrial pressure relief opening. In other embodiments a focused beam of light, such as a laser, may be directed towards the tissue. In still other embodiments other forms of electromagnetic energy may be employed to treat the tissue, such as ultraviolet light or microwave radiation. In still other embodiments a combination of any of these methods for treating the tissue near the intra-atrial pressure relief opening may be employed.

In embodiments depicted in FIGS. 2A to 2F where multiple electrodes or transducers are depicted it should be understood that any suitable number of electrodes or transducers may be used. In some embodiments, for example, two, three, four, five, or more Radio frequency electrodes may be located around the circumference of the dilation catheter in order to treat the tissue.

In some embodiments, the dilation catheter may not incorporate an energy delivering means. In these embodiments a secondary catheter that is similar to the dilation catheter, but does not require the conical dilating tip may be used. This secondary treatment catheter may make use of any of the various energy delivery means that are disclosed herein in order to treat the tissue surrounding the intra-atrial pressure relief opening. In this way the tasks of dilating the opening in the atrial septum and treating the intra-atrial pressure relief opening thus created may be separate tasks performed using separate catheters and still fall within the scope of the disclosure depicted in FIGS. 2A to 2F.

Figure 3:
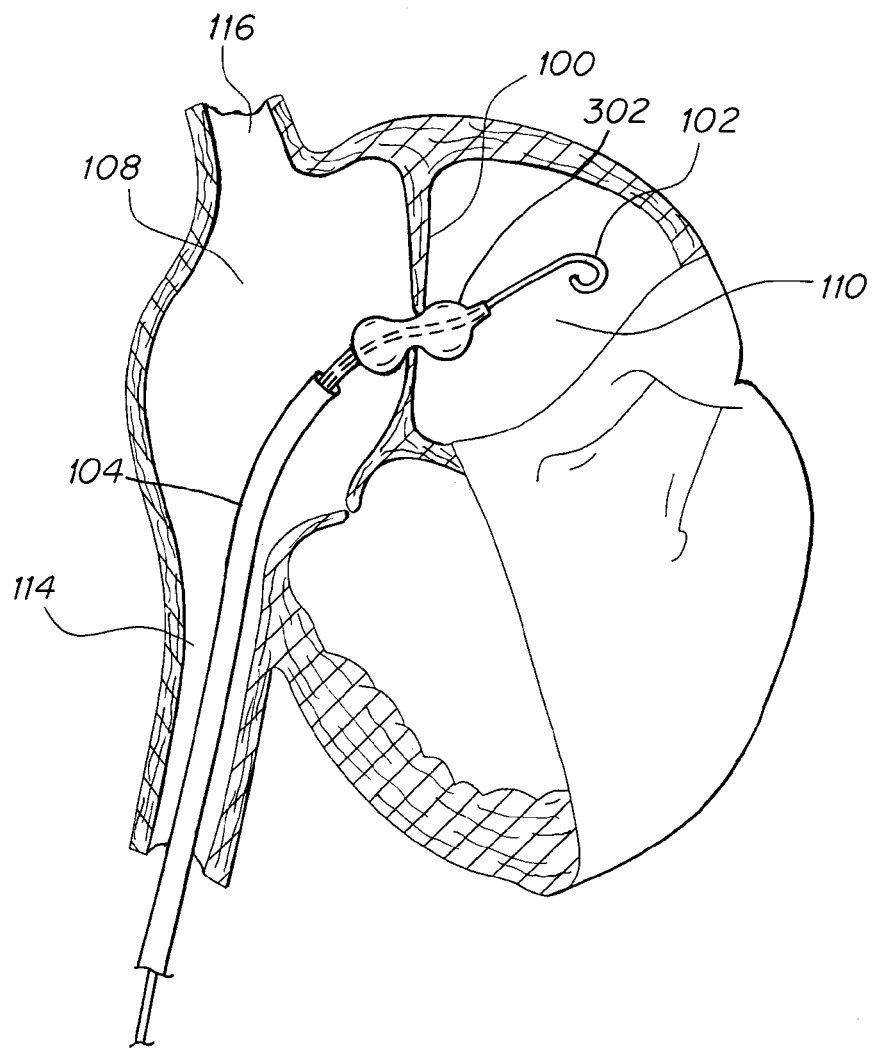
FIG. 3 is a cross sectional side view of an embodiment showing a catheter device implanted in a human heart with a dilation balloon.

Referring now to FIG. 3, additional embodiments are depicted. FIG. 3 shows a dilation balloon 302 which has been advanced to the atrial septum 100 and inflated. The balloon may be configured to be advanced over a wire 102, which has already penetrated the septum by conventional trans-septal wire delivery means, as are discussed earlier in this application. The opening in the atrial septum 100 may have been pre-dilated with a simple conical tip dilation catheter in order to make accessing the septum 100 with the balloon 302 easier. The balloon 302 is designed to dilate the opening in the atrial septum 100, thereby creating or enlarging an intra-atrial pressure relief opening of the desired therapeutic size. In some embodiments, the balloon 302 may dilate the opening in the atrial septum 100 up to a size between 4 mm and 8 mm. The balloon 302 optionally incorporates a means for treating the tissue surrounding the intra-atrial pressure relief opening. In some embodiments, the treatment may include a means for delivering energy to the tissue. In other embodiments, the treatment includes delivering a medication or combination of medications to the tissue.

The dilation balloon 302 of FIG. 3 may be shaped with an hour glass type shape where the diameter at the center of the balloon is smaller than the diameter at either end. Alternatively, the balloon 302 could be a simple cylinder, or be spherical or any other suitable shape. The balloon 302 may optionally feature stress concentrating or cutting elements on the surface of the balloon 302, in order to more easily dilate the opening in the septum 100. The balloon 302 may be non-compliant or compliant. The balloon catheter may include radio-opaque marking features to allow the user to appropriately place the balloon 302 at the septum 100 in order to dilate the septum 100 while inflating the balloon 302. Alternatively, the balloon 302 may be designed to be inflated entirely in the left atrium, and then may be drawn backwards by the user in order to position the balloon 302 and in order to dilate the septum 100. Methods of manufacturing and inflating balloon catheters are well established in the art.

Still referring to FIG. 3, where the balloon catheter is depicted as being advanced to the atrial septum 100 by tracking through the inferior vena cava 114. In alternative embodiments, the dilation balloon may access the atrial septum by other means, including from the jugular vein and through the superior vena cava 116. In addition, access to the atrial septum may be provided by other means, including through minimally invasive surgery, and through other major vessels in the body.

Figure 4A:
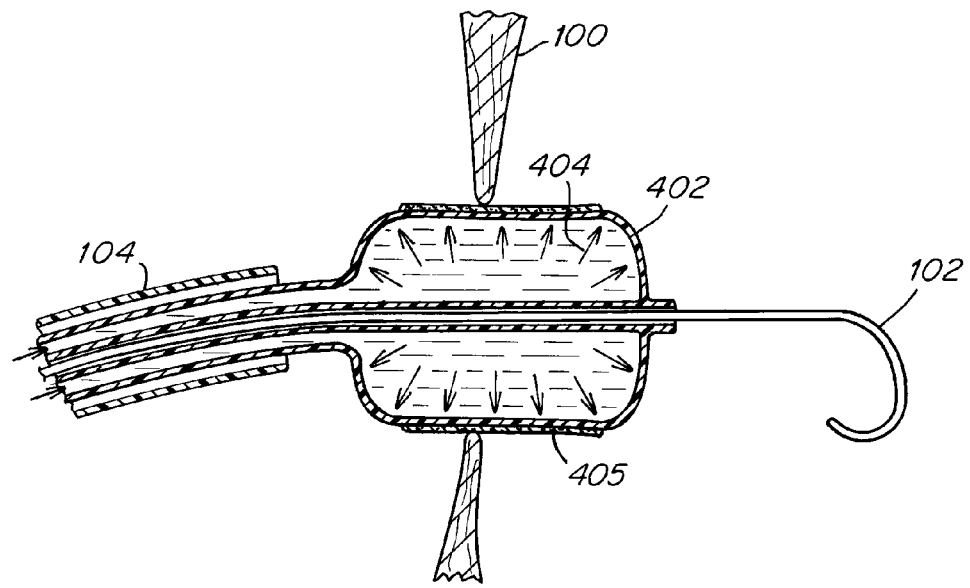
FIG. 4A is a cross sectional view of an embodiment depicting an inflated cylindrical dilation balloon coated with a drug.

Referring now to FIGS. 4A-4E, a series of balloon dilators featuring exemplary secondary treatment means are depicted. FIG. 4A shows a cross-sectional view of an inflated cylindrical dilation balloon 402. The dilation balloon 402 has crossed the atrial septum 100 by tracking over crossing wire 102. Arrows 404 depict the pressure of the fluid used to inflate the balloon. The balloon 402 is coated in a drug 405 which acts to slow the healing process of the body, such as an anti-proliferative drug or an immunosuppressive drug. In some embodiments, the drug coating may be one or a combination of the following drugs, paclitaxel, everolimus, sirolimus (rapamycin), zotarolimus, temsirolimus, doxorubicin, cyclophosphamide, or similar compounds. These drugs may also be applied in any other medically appropriate manner using suitable applicators.

In one embodiment, as mentioned below, the balloon may have a central lumen, shown in FIG. 4A, for deploying the balloon along a guide wire 102. One or more points along the central lumen or other portions of the balloon may include an echogenic or radiopaque feature for pin-point location of the balloon with respect to the atrial septum and the first opening and second larger opening created in the atrial septum. A portion of the outside or outer surface of the balloon may be coated with a medication or drug, as mentioned above, so that when the balloon is inflated, the outer surface and the medication are pressed against the opening made in the atrial septum. The balloon will typically be deployed by pushing the balloon down the guide wire within sheath 104. In some embodiments, the balloon itself will be deployed within a protective sheath (not shown) within outer sheath 104. The protective sheath acts to protect both the balloon and the medication on the outer surface of the balloon until the inflation balloon is in place. The balloon is then ready for inflation. Inflation of the balloon will act to enlarge the opening in the atrial septum and will also apply the medication to the now-exposed inner surface of the atrial septum (opening), which the balloon itself may have created. Alternatively, the enlarged opening in the atrial septum may be made by another method described below, while the balloon is used apply a medication. The medication, such as an anti-proliferative drug or an immunosuppressive drug, may be used to slow the healing process of the body. Examples of a drug include sirolimus, paclitaxel, zotarolimus, everolimus, silver nitrate, pyrimidine, methotrexate, azathioprine, dactinmycin, formalin, formaldehyde and ethanol.

In still other embodiments, the coating contains a radiation source similar to that used in brachytherapy. In some embodiments, the balloon 402 may be shaped in order to maximize the surface contact between the medicinal coating 405, as shown in FIG. 4A, and the intra-atrial pressure relief opening created by the balloon 402. In some embodiments, the balloon 402 featuring the medicinal coating 405 may also feature ribs, protrusions, or other cutting elements in order to further increase the surface area available to be treated by the coating. In some embodiments, the balloon is inflated in the septum 100 and then drawn back proximally or advanced distally or simply rotated in order to encourage the adhesion of the medicinal coating 405 onto the tissue surrounding the intra-atrial pressure relief opening.

Figure 4B:
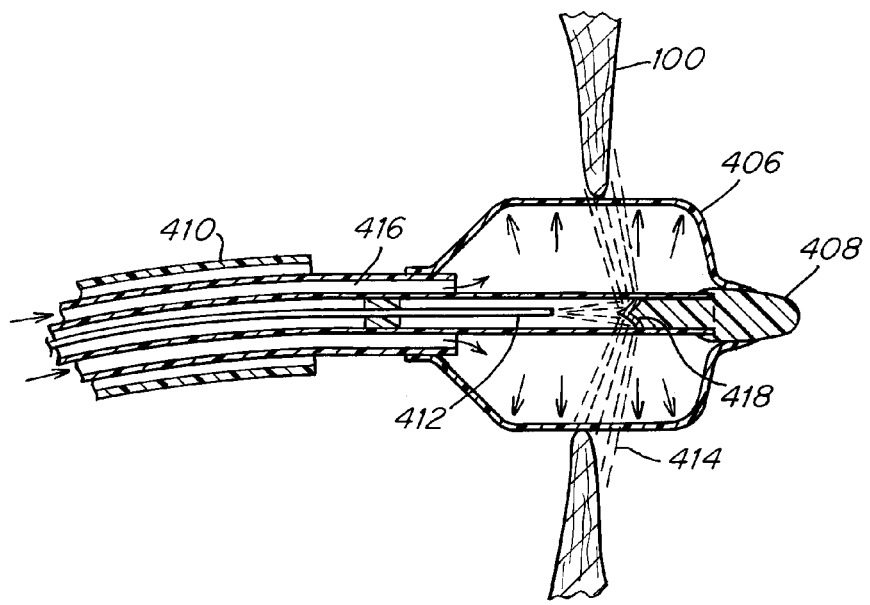
FIG. 4B is a cross sectional view of an embodiment depicting a dilation balloon with an optical fiber for delivering visible light energy of a desired intensity.

FIG. 4B shows a dilation balloon 406 is configured to create an intra-atrial pressure opening by dilating an opening created in the atrial septum 100 by conventional means. In FIG. 4B, the balloon 406 is depicted with a plug 408 closing off the distal end, and therefore is not delivered over a wire. As disclosed above, and in alternative embodiments, the dilation balloon may also be configured with a central through lumen and be designed to be delivered over the wire. The balloon catheter is shown nested inside an optional delivery sheath 410, which may be used to maintain the proper position of the devices relative to the opening in the atrial septum.

The balloon 406 includes an energy delivering means, incorporating a flexible optical fiber 412, which may be used to transmit visible light of a desired intensity. The visible light is represented by the dashed lines 414 in FIG. 4B. The optical fiber 412 is positioned in a center passageway that does not communicate with the annular passageway 416 for the inflation fluid. In some embodiments, the inflation fluid is chosen which has an especially high light transmission. In some embodiments, the inflation fluid is distilled water, de-ionized water, or a gas, for example, air or nitrogen. The optical fiber 412 emits the light energy inside the balloon 406 in a direction that is substantially axial to the treatment device. A 3-dimensionally curved mirror 418 is positioned in line with the optical fiber 412. The curved mirror 418 is configured to reflect the light energy in a radial direction. The curved mirror 418 is also configured to focus the light into a thin band in the axial direction by acting as a lens. The light source and the curved mirror 418 therefore direct significant light energy to the tissue surrounding the atrial septum 100 generating considerable heat, thereby ablating or otherwise damaging the tissue near the intra-atrial pressure relief opening.

Figure 4C:
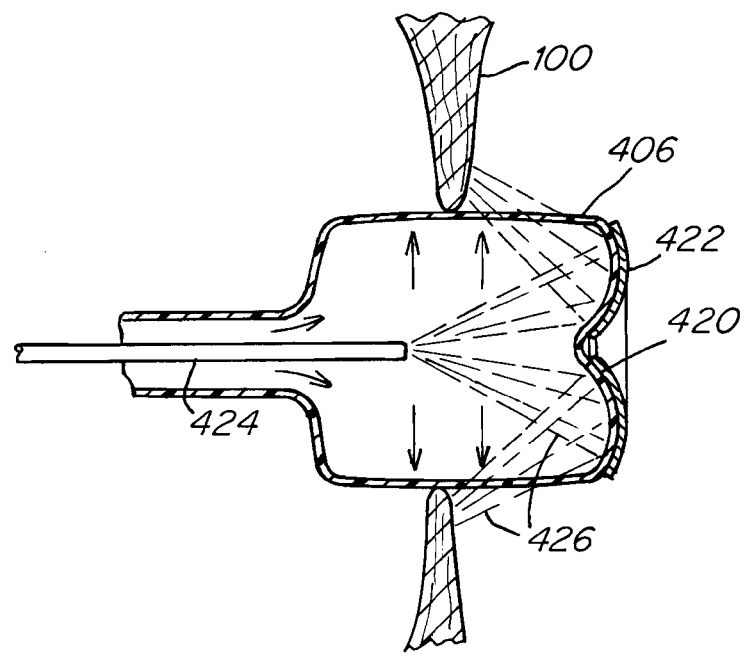
FIG. 4C is a cross sectional view of an embodiment depicting a dilation balloon with optical fiber, covered with reflective coating at its distal end for delivering visible light energy.

FIG. 4C depicts a dilation balloon 406 configured to create an intra-atrial pressure opening by dilating an opening created in the atrial septum 100 by conventional means. The balloon 406 is similar to the balloon which is depicted in FIG. 4B except that the distal end 420 of the balloon is covered by a reflective coating 422. The balloon 406 is further configured so that when fully inflated the distal end of the balloon is shaped like a concave lens. The lens shape coupled with the reflective coating 422 turns the dilation balloon 406 itself into a means for reflecting and focusing light. The light is supplied by an optical conduit 424 which may be a single optical fiber or a cable of optical fibers. The path the light takes is depicted by a series of dashed lines 426 which roughly approximate the shape of the wave of light being emitted by the optical fibers. The light can be described as exiting the optical fiber and traveling to the reflective distal end, where it bounces and is focused in an angular fashion towards the tissue surrounding the intra-atrial pressure relief opening. After being reflected at the distal end of the balloon 406, the light can further be described as a hollow cone of ever increasing intensity. In this way the dilation balloon 406 of FIG. 4C represents a means of ablating tissue in the vicinity of the intra-atrial pressure relief opening by means of focusing high intensity light at the tissue.

Figure 4D:
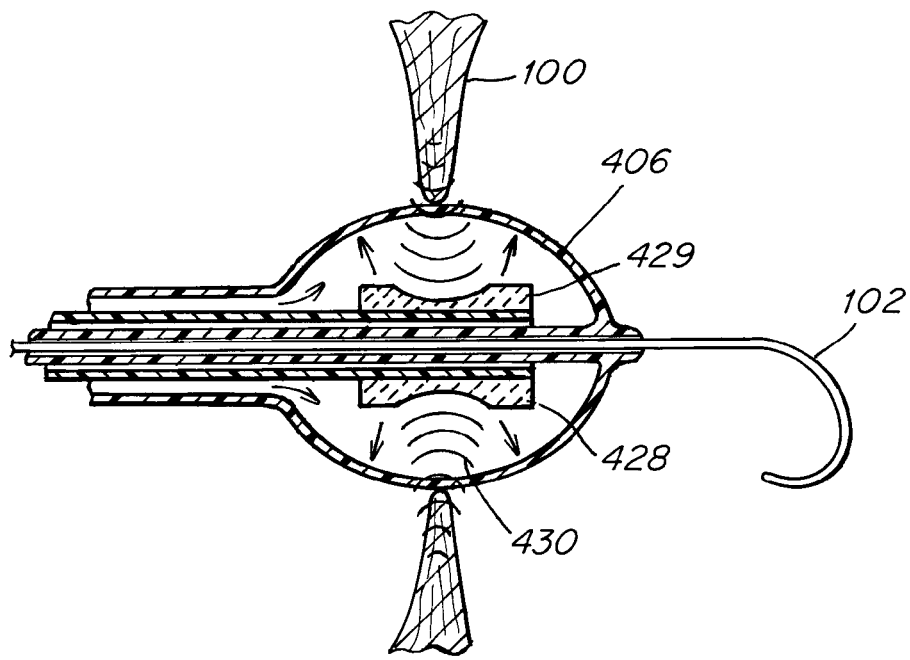
FIG. 4D is a cross sectional view of one an embodiment depicting a dilation balloon with plurality of piezoelectric ultrasound transducer arrays as a means for delivering ultrasound energy.

Turning now to FIG. 4D a dilation balloon 406 is shown having been inflated and having dilated an opening in an atrial septum 100. As with other embodiments, the original puncture in the atrial septum 100 can be created by conventional means described herein and also well known in the art. In addition, the original puncture in the atrial septum 100 may be pre-dilated by a simple dilation catheter prior to inserting the dilation balloon 406 and applying treatment. The balloon 406 is configured to be delivered over a crossing wire 102, although in alternative embodiments the balloon 406 may be delivered without the aid of a crossing wire 102.

Incorporated in the balloon of FIG. 4D is a plurality of piezoelectric ultrasound transducer arrays 428, 429 which are similar to the transducer arrays discussed above and illustrated in FIG. 2E. The transducer arrays 428, 429 are configured to emit high intensity focused ultrasonic energy in a generally radial direction across most of the circumference of the balloon 406. The ultrasonic energy is depicted as a series of curved lines 430. In alternative embodiments, the ultrasound transducer arrays may be arranged so as to comprise a phased array in order to focus the ultrasonic energy. A similar phased array is also disclosed above, and is depicted in FIG. 2D. The transducer array represents a means for delivering energy to the tissue in order to ablate or otherwise destroy the tissue and slow down the natural healing process of the body.

Figure 4E:
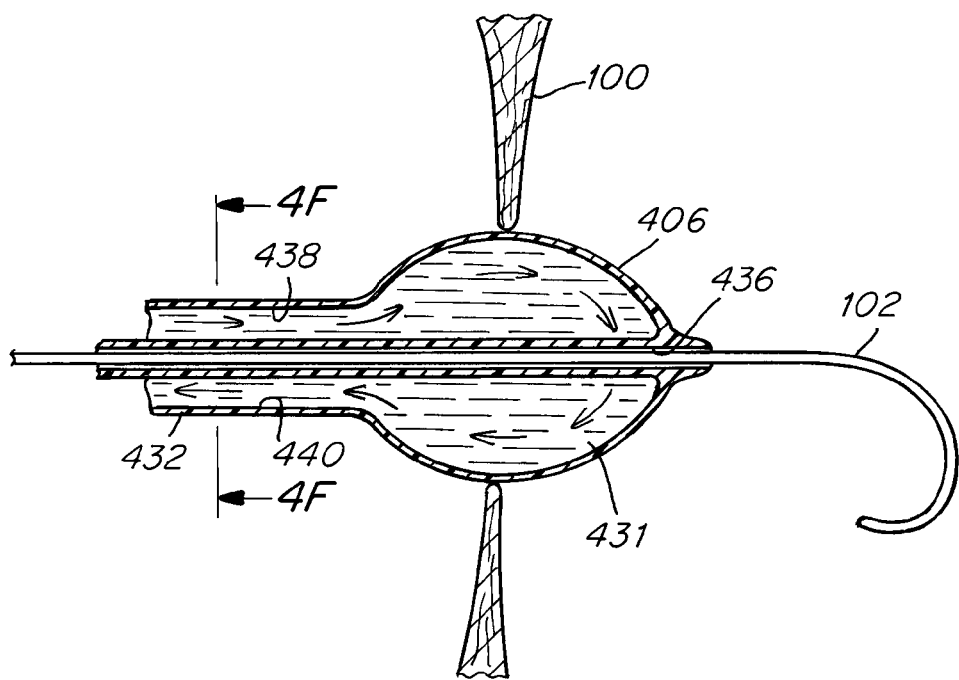
FIGS. 4E-4F are a cross sectional view of an embodiment depicting a dilation balloon with two fluid passageways for delivering energy.
Figure 4F:
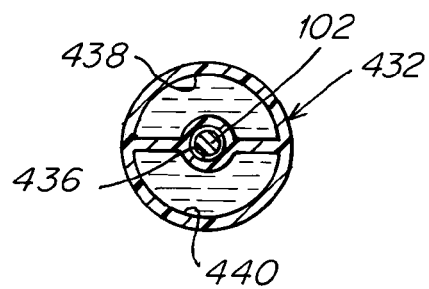

Turning now to FIG. 4E another dilation balloon 406 is depicted. The balloon 406 is configured to be advanced to a small puncture opening in the atrial septum 100 and inflated as shown. The balloon 406 is further configured to be advanced over a crossing wire 102. Once inflated the balloon 406 defines an annular space 431, which is configured to allow fluid to flow around the circumference. Proximal to the balloon 406 the catheter features a shaft with a three lumen cross section 432, as shown in the cross sectional detail of FIG. 4F. FIG. 4F is a cross sectional view taken along line 4F-4F in FIG. 4E. The location of the cross-sectional detail on the proximal shaft is represented by a dotted line 434. In this cross-sectional view the center lumen 436 is configured to accept the crossing wire. One lobed region 438 represents an inlet passage for the inflation fluid, while the other lobed region 440 represents an outlet passage for the inflation fluid. The two fluid passageways are separately connected on the proximal end to an external pump.

The dilation balloon catheter of FIGS. 4E-4F is used in two stages. First the balloon 406 is inflated by closing off the outlet channel 440 and forcing a heat transfer fluid through the inlet channel 438, thereby inflating the balloon 406. When the balloon is satisfactorily inflated the atrial septum 100 puncture is dilated and an intra-atrial pressure relief opening is thereby created. After fully inflating the balloon 406 the heat transfer fluid is forced to circulate through the annular space 431 of the balloon 406. This is accomplished by forcing additional heat transfer fluid through the inlet lumen 438, and allowing sufficient fluid to flow through the outlet lumen 440. The backpressure on the outlet lumen 440 is controlled by the external pump, for example, by means of a gear pump with friction clutch. In this way sufficient pressure to keep the balloon 406 inflated is supplied while there is still considerable fluid flow through the balloon 406. The heat transfer fluid circulating through the balloon 406 may be any of the same fluids disclosed above. The heat transfer fluid flowing through the balloon allows for the transferring of energy to or from the tissue in order to damage or ablate the tissue surrounding the atrial an intra-atrial pressure relief opening. In this way the dilation balloon catheter of FIG. 4E represents a means of creating an intra-atrial pressure relief opening and treating the tissue surrounding the opening in order to prolong the patency of the opening.

The various embodiments for applying a treatment to the tissue surrounding the intra-atrial pressure relief opening as depicted in FIGS. 4A-4F are not intended to be an exhaustive list of the treatment options available. For example, in additional embodiments, a balloon may be configured with a microwave energy emitter. In other embodiments the balloon may incorporate a network of electrodes for heating the tissue surrounding the intra-atrial pressure relief opening. In other embodiments a balloon may include a coating on the internal diameter which when mixed with the inflation fluid undergoes a highly exothermic or endothermic reaction, thereby heating or cooling the tissue. Examples of these fluids include water and saline. In other embodiments, the balloon may be coated in a fixative or biocompatible glue, which fixes the tissue and impedes the normal healing response of the body. Examples include pyrimidine, methotrexate, azathioprine and dactinmycin. In still other embodiments, the balloon includes pores designed to exude a small amount of ethyl alcohol, thereby ablating the tissue surrounding the intra-atrial pressure relief opening.

Figure 5:
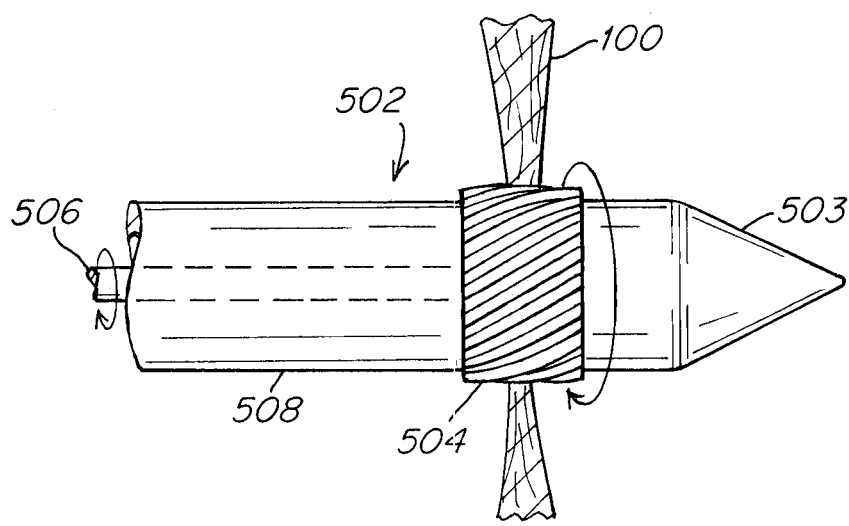
FIG. 5 is a side view of an embodiment depicting a catheter configured to abrade or scrape septum surrounding an intra-atrial pressure relief opening.

Turning now to FIG. 5, additional embodiments are depicted. A dilation catheter 502 including a conical distal tip 503 is shown. The catheter 502 is shown having already dilated a punctured opening in an atrial septum 100, thereby creating an intra-atrial pressure relief opening. Incorporated in the dilation catheter shaft 508 is a textured or ribbed cylindrical section 504, which is rotatably coupled to the catheter shaft 508. The ribbed section of the catheter shaft 508 is configured to abrade or scrape the tissue surrounding the intra-atrial pressure relief opening in order to encourage the formation of thickened scar tissue. In alternative embodiments the ribbed section of the catheter shaft 508 may instead by replaced by a section of catheter shaft 508 which has an abrasive material fixed to it, such as crimped stainless steel wires or sharpened glass beads.

Still referring to FIG. 5, the ribbed section of the catheter shaft 508 is coupled to a torque transmission member 506. The torque transmission member 506 may be any suitably flexible elongate member which is capable of transmitting torque over the length of the catheter shaft 508. In some embodiments, the torque transmitting member 506 is a trifilar drive shaft, where each layer of filars is turned in opposing directions. The torque transmission member 506 may be coupled to an external drive source, or it may instead by rotated manually by the user, in order to abrade the tissue surrounding the intra-atrial pressure relief opening. The abrasion and the friction between the ribbed sections of the catheter 502 together encourage the formation of a thick scar tissue, which in turn slows down the healing process of the body and helps to maintain the patency of the pressure related opening. In this way dilation catheter 502 represents a means for creating an intra-atrial pressure relief opening and prolonging its patency.

In alternative embodiments as depicted in FIG. 5, the textured section of the shaft may be fixed relative to the rest of the catheter shaft 508. In this case the user may simply advance and retract the catheter device 502 axially in rapid succession, thereby abrading the tissue near the intra-atrial pressure relief opening. An external drive source may be used to actuate the catheter 502 in this way, or the user may simple actuate the catheter 502 by hand.

Other techniques may also be used for creating an opening in the atrial septum of a patient in order to provide intra-atrial pressure relief. One such technique is depicted in FIGS. 6A-6H. In this technique, a wire guide is advanced to the area of interest near the location where the atrial septum opening is desired. As is well known to those having skill in the art, the wire guide may be equipped with a radiopaque tip or echogenic features (not shown) for better visibility by monitoring equipment and medical personnel during the procedure. Some wire guides have a rounded distal end in order to prevent trauma to the patient, some have a penetrating end, such as the one discussed above with respect to FIG. 1. The initial penetration, as described further with respect to FIG. 1 may then be followed up with cutting instruments to enlarge the opening.

In the cross-sectional view of FIG. 6A, the wire guide 102 in sheath 104 has penetrated the atrial septum 100, creating an initial opening 118. FIG. 6B is a plan view that depicts the relative size of the initial opening 118 in the atrial septum 100, as seen from a viewing point in the left atrium. In FIG. 6C, the opening has been expanded sufficiently to allow insertion of a retaining and reaction device 120 with legs 122 via sheath 104. FIG. 6D again depicts the deployed legs 122 from a viewing point in the left atrium. The reaction and retaining device 120 may comprise a series of struts 124 and apices 126, in a manner very similar to the legs depicted in U.S. Pat. No. 8,043,360, assigned to the assignee of the present application and incorporation herein by reference in its entirety. The intention of the procedure is to prepare an opening in the atrium septum of diameter 128, as seen in FIG. 6F. Diameter 128 may be from about 5 mm to about 10 mm, depending on instructions from the patient's physician or health care provider. The legs 122 should extend a little less than the intended final diameter or dimension of the opening 128. As will be recognized by those having skill in the art, the legs will act to retain the tissue which is removed from the septal wall. In some techniques, the wire guide 102 will be left in place to also retain the tissue. While wire guide 102 will generally not be sufficient for removal of the tissue, the wire guide will act to prevent movement of the tissue away from the general area of the septal wall.

Once the legs are in place, an RF probe is inserted into the area of interest near the septal wall using sheath 104, as shown in FIG. 6E. RF probe 130 is connected to a source of power via wire 132, in a manner similar to that discussed above for FIG. 2A. The FIG. 6F depicts a plan view of the situation, again from a viewing point in the left atrium. The legs with struts 124 and apices 126 are deployed within a roughly circular area 128, which is the area from which tissue is to be removed. The RF probe 130 may be a circular probe as depicted in the figure. The probe is energized to ablate tissue and to separate the tissue from the atrial septum. Alternatively, the probe may comprise an arc or a short length. In this situation, the probe is sequentially moved or rotated through the roughly circular pattern until the ablation has been completed and the tissue is ready for removal. In one embodiment, the system is unipolar and is designed to shut down when ablation has proceeded sufficiently that when RF current or voltage reaches legs 124. In other techniques, there may be a delay after current or voltage is detected, to insure that penetration through the tissue is complete. This technique has the advantage that the location of 5-10 mm diameter-sized tissue is in the control of the surgeon and the surgical team at all times during the procedure.

As noted above, the RF probe may be unipolar, with the patient protected by a grounding pad. Alternatively, a bi-polar technique may be used, with a grounding electrode on the left atrial side of the patient or externally on the patient. In one technique, the RF probe (first electrode) and the grounding probe (second electrode) may be positioned on opposite sides of the atrial septum. Their locations may then be verified before the probe is energized and ablation begins. This technique may be used for a circular RF probe or for a smaller probe, in the general form of an arc or a short length. The procedure continues until ablation is completed and the tissue is ready for removal.

When ablation is complete, the separated or removed tissue 134 may be retained by device 120 and legs 122 for removal or extraction from the patient, as shown in FIG. 6G. FIG. 6H depicts the removed tissue. In one embodiment, device 120 is sufficient for extraction, and tissue 134 with initial opening 118 may be extracted from the patient by retracting device 120 through sheath 104. In other embodiments, tissue 134 may be retained by wire guide 102 and a grasper advanced through sheath 104 to grasp and extract the tissue, as disclosed in U.S. patent application Ser. No. 12/954,468, co-owned by the assignee of the present application, and incorporated by reference in its entirety.

Figures 7A, 7B:
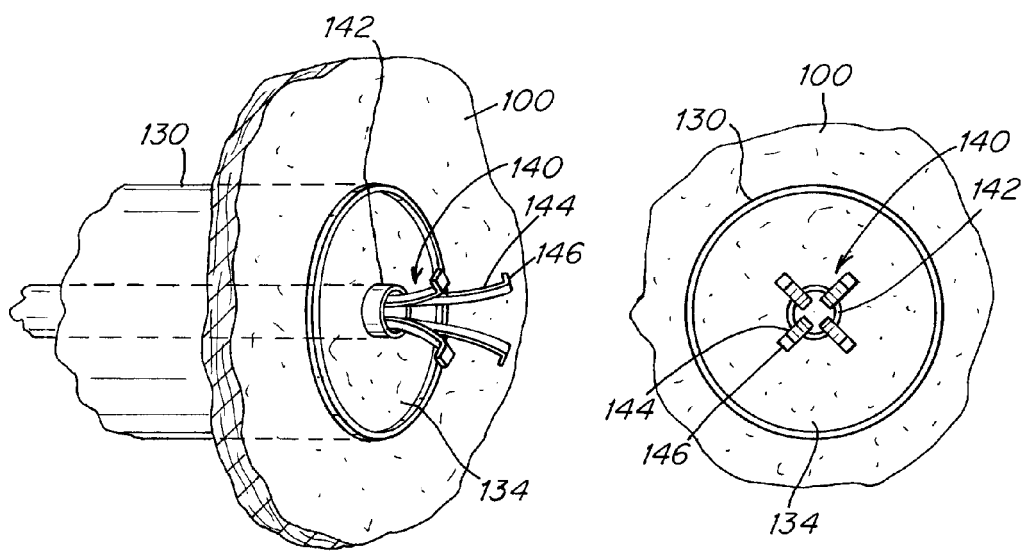
FIGS. 7A-7B depict a grasper suitable for removing separated septal-wall tissue.

An example of a suitable grasper 140 with retaining prongs 144 is depicted in FIGS. 7A-7B. The grasper 140 is advanced through sheath 104 to the area of interest, near the septal wall. The grasper is deployed when sufficiently near the tissue 134 by advancing the grasper from grasper sheath 142 so that tips 146 are spread and are able to grasp the tissue which has been separated from the patient's atrial septum. The tips 146 engage tissue 134 when they are sufficiently close that when the tips are refracted into grasper sheath 142, the tips 146 engage the tissue and are able to securely retain the tissue. The separated tissue is then extracted or removed from the patient through sheath 104.

In addition to the above disclosed embodiments, the tissue may be treated by any combination of the above discussed treatment options. In these embodiments, the steps of dilating the puncture opening in the atrial septum and treating the tissue to slow down the healing process of the body may be spread out over a series of similar devices.

In another embodiment, a method is provided for treating elevated pulmonary venous pressure and elevated left atrial pressure caused by heart failure. The method includes creating an intra-atrial pressure relief opening by using any of the devices or means disclosed herein. The method further includes treating the tissue in the vicinity of the intra-atrial pressure relief opening with a treatment operation. The secondary treatment operation includes any of the above mentioned treatment means or devices, including the use of energy to ablate the tissue or drugs to delay the healing response of the body.

While reference has been made to various drawings and embodiments, it should be understood that certain substitutions, additions, and exchanges may be made by those skilled in the art while still remaining within the scope of the invention. The scope of the invention should therefore be defined by the attached claims:

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments are described herein, including the best mode known to the inventors for carrying out the invention. Variations of those embodiments may become apparent to those of ordinary skill in the art upon reading the foregoing description. Skilled artisans will use such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the claims unless otherwise indicated herein or otherwise clearly contradicted by context.

What is claimed is:

1. A method for normalizing elevated blood pressure in a heart chamber, the method comprising:
   penetrating an atrial septum between a right atrium and a left atrium of a heart to create an opening in the atrial septum;
   increasing the opening to a larger size to create an intra-atrial pressure relief opening;
   after the increasing step, treating tissue near the intra-atrial pressure relief opening to slow a natural healing process of the tissue to maintain patency of the intra-atrial pressure relief opening without implanting a stent or valve in the intra-atrial pressure relief opening; and
   permitting blood to flow from the left atrium to the right atrium through the intra-atrial pressure relief opening to reduce left atrial pressure.

2. The method according to claim 1, wherein the treating step comprises delivering energy to the tissue near the intra-atrial pressure relief opening.

3. The method according to claim 1, wherein the treating step comprises delivering medication or a combination of medications to the tissue near the intra-atrial pressure relief opening.

4. The method according to claim 1, wherein the treating step comprises delivering an anti-proliferative or immunosuppressive drug to the tissue near the intra-atrial pressure relief opening.

5. The method according to claim 1, wherein the treating step comprises ablating, heating or cooling the tissue near the intra-atrial pressure relief opening.

6. The method according to claim 1, wherein the treating step comprises providing radiation energy to the tissue near the intra-atrial pressure relief opening.

7. The method according to claim 1, wherein the treating step comprises exuding ethyl alcohol from a balloon catheter into the tissue near the intra-atrial pressure relief opening.

8. The method according to claim 1, wherein the increasing step comprises enlarging the opening with a balloon catheter or with a conical distal tip of a catheter.

9. The method of claim 1, wherein the increasing step comprises using RF ablation.

10. The method of claim 1, wherein the increasing step comprises creating an intra-atrial pressure relief opening having a diameter from about 5 mm to about 10 mm.

11. The method of claim 1, wherein the treating step comprises
   preparing a balloon with a medication on an outer surface of the balloon;
   deploying the balloon within the intra-atrial pressure relief opening using a sheath; and
   inflating the balloon to apply the medication to an inner surface of the intra-atrial pressure relief opening.

12. The method of claim 1, wherein the treating step comprises applying an adhesive, a fixative or an adhesion prevention substance to the tissue near the intra-atrial pressure relief opening.

13. The method of claim 1 wherein the increasing step comprises removing tissue from the atrial septum.

14. The method of claim 1 wherein the increasing step comprises inserting a retracting device from the right atrium through the atrial septum into the left atrium and grasping tissue with the retracting device.

15. The method of claim 14, wherein the retracting device comprises a plurality of legs, each leg comprising at least two struts and one apex.

16. A method for normalizing elevated blood pressure in a heart chamber, the method comprising:
    creating an intra-atrial pressure relief opening in an atrial septum between a right atrium and a left atrium, the intra-atrial pressure relief opening having a diameter from about 5 mm to about 10 mm;
    treating tissue near the intra-atrial pressure relief opening to slow a natural healing process of the tissue to maintain patency of the intra-atrial pressure relief opening without implanting a stent or valve in the intra-atrial pressure relief opening; and
    permitting blood to flow from the left atrium to the right atrium through the intra-atrial pressure relief opening to reduce left atrial pressure.

17. The method according to claim 16, wherein the treating step comprises delivering energy to the tissue near the intra-atrial pressure relief opening.

18. The method according to claim 16, wherein the treating step comprises delivering medication or a combination of medications to the tissue near the intra-atrial pressure relief opening.

19. The method according to claim 16, wherein the treating step comprises delivering an anti-proliferative or immunosuppressive drug to the tissue near the intra-atrial pressure relief opening.

20. The method according to claim 16, wherein the treating step comprises ablating, heating or cooling the tissue near the intra-atrial pressure relief opening.

21. The method according to claim 16, wherein the treating step comprises providing radiation energy to the tissue near the intra-atrial pressure relief opening.

22. The method according to claim 16, wherein the treating step comprises exuding ethyl alcohol from a balloon catheter into the tissue near the intra-atrial pressure relief opening.

23. The method of claim 16, wherein the treating step comprises applying an adhesive, a fixative or an adhesion prevention substance to the tissue near the intra-atrial pressure relief opening.

24. The method according to claim 16, wherein the creating step comprises inserting a balloon catheter or a conical distal tip of a catheter into the atrial septum.

25. The method of claim 16, wherein the creating step comprises using RF ablation.

26. The method of claim 16 wherein the creating step comprises removing tissue from the atrial septum.

27. The method of claim 16 wherein the creating step comprises inserting a retracting device from the right atrium through the atrial septum into the left atrium and grasping tissue with the retracting device.

28. The method of claim 27, wherein the retracting device comprises a plurality of legs, each leg comprising at least two struts and one apex.

\* \* \* \* \*